United States Patent
Thomas et al.

(12) 
(10) Patent No.: US 6,285,450 B1
(45) Date of Patent: *Sep. 4, 2001

(54) BLOOD CENTRIFUGATION DEVICE WITH MOVABLE OPTICAL READER

(76) Inventors: Bradley S. Thomas, 21 Norwick Cir., Timonium, MD (US) 21093; Michael A. Kelly, 3125 Wheatlyn Rd., York, PA (US) 17402; Michael R. Walters, 12852 Sand Dollar Way, Baltimore, MD (US) 21220; Edward M. Skevington, 2031 Stewartstown Rd., Stewartstown, PA (US) 17363; Paul F. Gaidis, 26 John Randolf Dr., New Freedom, PA (US) 17349

( * ) Notice: Subject to any disclaimer, the term of this patent is extended or adjusted under 35 U.S.C. 154(b) by 0 days.

This patent is subject to a terminal disclaimer.

(21) Appl. No.: 09/033,368

(22) Filed: Mar. 2, 1998

(51) Int. Cl.$^7$ .................................................. G01N 21/01
(52) U.S. Cl. .............................................. 356/244; 356/36
(58) Field of Search ................................... 356/213, 244, 356/36, 37, 38

(56) References Cited

U.S. PATENT DOCUMENTS

| | | |
|---|---|---|
| 3,199,775 | 8/1965 | Drucker . |
| 3,741,011 | 6/1973 | Seybold . |
| 3,955,890 | 5/1976 | Bessis et al. . |
| 4,027,660 | 6/1977 | Wardlaw et al. . |
| 4,077,396 | 3/1978 | Wardlaw et al. . |
| 4,082,085 | 4/1978 | Wardlaw et al. . |
| 4,156,570 | 5/1979 | Wardlaw . |
| 4,428,669 | 1/1984 | Bessis . |
| 4,479,720 | 10/1984 | Mochida et al. . |
| 4,555,183 | 11/1985 | Thomas . |
| 4,558,947 | 12/1985 | Wardlaw . |

(List continued on next page.)

OTHER PUBLICATIONS

Stephen C. Wardlaw, MD, et al., "Quantitative Buffy Coat Analysis—A New Laboratory Tool Functioning as a Screening Complete Blood Cell Count", *Journal of the American Medical Association*, vol. 249, Feb. 4, 1983, pp. 617–620.

Robert L. Sallitt, et al., "Evaluation of Leukocyte Differential Counts on the QBC® Centrifugal Hematology Analyzer According to NCCLS Standard H20–T", *Blood Cells*, vol. 11, 1986, pp. 281–294.

QBC® Centrifugal Hematology Control Kit Brochure, Becton Dickinson and Company, 1988.

QBC® Autoread™ Centrifugal Hematology System Brochure, Becton Dickinson and Company, 1991.

QBC® Centrifuge System Centrifuge Model 424740 Brochure, Becton Dickinson and Company, Aug., 1993.

QBC® Centrifugal Hematology Control Brochure, Becton Dickinson and Company, 1995.

QBC® Hematology Control Assay, Becton Dickinson and Company, 1996.

QBC® Auotread™ Plus Brochure, Becton Dickinson and Company, 1996.

QBC® Hematology Control Instructions for Use, Becton Dickinson and Company, published prior to 1998.

Primary Examiner—Frank G. Font
Assistant Examiner—Layla Lauchman
(74) Attorney, Agent, or Firm—Bruce S. Weintraub

(57) ABSTRACT

A centrifuge device that is used to centrifuge a fluid sample, such as a blood sample, to separate the fluid sample into its various component layers, and which is capable of measuring the length of the component layers to calculate cell counts for each layer. The centrifuge device includes a rotor assembly for rotating and thus centrifuging the fluid sample, and a movable optical reader device for reading the cell layers in the centrifuged sample. The centrifuge device is capable of accurately controlling the reading of the centrifuged sample based on the orientation of the rotor, so that the rotor can continue to rotate the centrifuged sample while the readings are being taken.

24 Claims, 24 Drawing Sheets

U.S. PATENT DOCUMENTS

| | | |
|---|---|---|
| 4,567,754 | 2/1986 | Wardlaw et al. . |
| 4,774,965 | 10/1988 | Rodriguez et al. . |
| 4,823,624 | 4/1989 | Rodriguez et al. . |
| 4,848,917 | 7/1989 | Benin et al. . |
| 5,195,825 | 3/1993 | Ringrose . |
| 5,380,087 | 1/1995 | Haber et al. . |
| 6,002,474 * | 12/1999 | Thomas et al. ................... 356/244 |

* cited by examiner

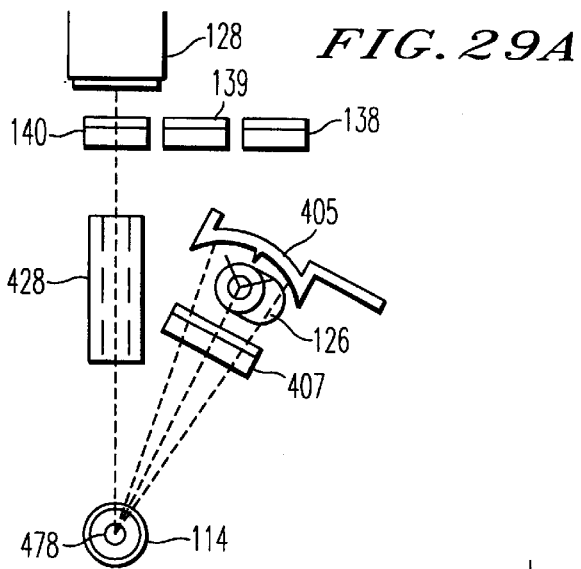
FIG. 29A
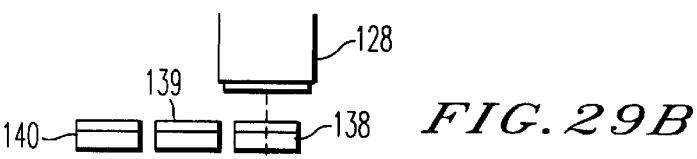
FIG. 29B
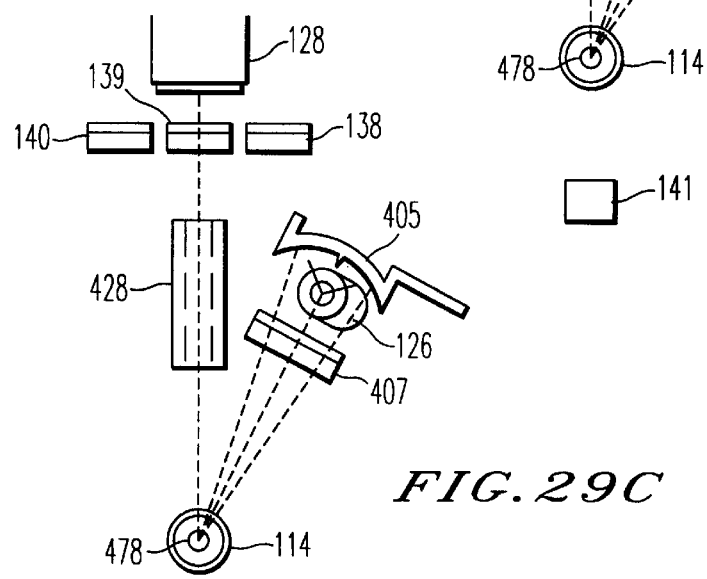
FIG. 29C

BLOOD CENTRIFUGATION DEVICE WITH MOVABLE OPTICAL READER

CROSS-REFERENCE TO RELATED APPLICATIONS

Related subject matter is disclosed and claimed in a U.S. patent application of Stephen C. Wardlaw entitled "Assembly for Rapid Measurement of Cell Layers", Ser. No. 08/814,536, filed on Mar. 10, 1997 which has issued as U.S. Pat. No. 5,889,584; in a U.S. patent application of Stephen C. Wardlaw entitled "Method for Rapid Measurement of Cell Layers", Ser. No. 08/814,535, filed on Mar. 10, 1997 which has issued as U.S. Pat. No. 5,888,184; in a U.S. patent application of Michael R. Walters entitled "Centrifugally Actuated Tube Rotator Mechanism" (Ser. No. 08/918,437 which has since been abandoned, however a continuation-in-part of this application was filed, Ser. No. 09/210,332, which has issued as U.S. Pat. No. 6,135,940); in U.S. patent applications of Michael A. Kelly, Edward G. King, Bradley S. Thomas and Michael R. Walters entitled "Disposable Blood Tube Holder" and "Method of Using Disposable Blood Tube Holder" Ser. Nos. 09/033,373 and 09/033,119, filed on even date herewith which have issued as U.S. Pat. Nos. 6,080,366 and 6,074,883, respectively; in U.S. patent applications of Michael R. Walters entitled "Inertial Tube Indexer" and "Method for Using Inertial Tube Indexer" Ser. Nos. 09/032,931 and 09/033,367, filed on even date herewith wherein Ser. No. 09/033,367 has since issued as U.S. Pat. No. 6,120,429; and in U.S. patent application of Bradley S. Thomas, entitled "Flash Tube Reflector With Arc Guide" Ser. No. 09/032,935, filed on even date herewith which has issued as U.S. Pat. No. 6,030,086 all of said applications being expressly incorporated herein by reference.

BACKGROUND OF THE INVENTION

The present invention relates generally to a centrifuge device which is capable of centrifuging a blood sample contained in a blood tube and also reading the blood component layers formed in the blood tube as a result of the centrifugation. More particularly, the present invention relates to a centrifuge device having a movable optical reader device that is capable of moving with respect to the blood tube to optically read the blood component layers in the entire centrifuged blood sample while the blood sample is being spun by the rotor of the centrifuge device, and further having an indexing mechanism which rotates the blood tube in the rotor about an axis substantially corresponding to the longitudinal axis of the blood tube, while the rotor is spinning the blood tube, so that the component layers can be read by the optical reader device from different locations about the circumference of the blood tube. The centrifuge device further has detectors for detecting the centrifugation of the rotor to control the reading of the blood tube, and the loading and unloading of the blood tube in the rotor.

As part of a routine physical or diagnostic examination of a patient, it is common for a physician to order a complete blood count for the patient. The patient's blood sample may be collected in one of two ways. In the venous method, a syringe is used to collect a sample of the patient's blood in a test tube containing an anticoagulation agent. A portion of the sample is later transferred to a narrow glass sample tube such as a capillary tube. The open end of the sample tube is placed in the blood sample in the test tube, and a quantity of blood enters the sample tube by capillary action. The sample tube has two fill lines at locations about its circumference, and the volume of blood collected should reach a level in the sample tube between the two fill lines. In the capillary method, the syringe and test tube are not used, and the patient's blood is introduced directly into the sample tube from a small incision made in the skin. In either case, the sample tube is then placed in a centrifuge, such as the Model 424740 centrifuge manufactured by Becton Dickinson and Company.

In the centrifuge, the sample tube containing the blood sample is rotated at a desired speed (typically 8,000 to 12,000 rpm) for several minutes. The high speed centrifugation separates the components of the blood by density. Specifically, the blood sample is divided into a layer of red blood cells, a buffy coat region consisting of layers of granulocytes, mixed lymphocytes and monocytes, and platelets, and a plasma layer. The length of each layer can then be optically measured, either manually or automatically, to obtain a count for each blood component in the blood sample. This is possible because the inner diameter of the sample tube and the packing density of each blood component is known, and hence the volume occupied by each layer and the number of cells contained within it can be calculated based on the measured length of the layer. Exemplary measuring devices that can be used for this purpose include those described in U.S. Pat. Nos. 4,156,570 and 4,558,947, both to Stephen C. Wardlaw, and the QBC® "AUTOREAD" centrifuged hematology system manufactured by Becton Dickinson and Company.

Several techniques have been developed for increasing the accuracy with which the various layer thickness in the centrifuged blood sample can be determined. For example, because the buffy coat region is typically small in comparison to the red blood cell and plasma regions, it is desirable to expand the length of the buffy coat region so that more accurate measurements of the layers in that region can be made. As described in U.S. Pat. Nos. 4,027,660, 4,077,396, 4,082,085 and 4,567,754, all to Stephen C. Wardlaw, and in U.S. Pat. No. 4,823,624 to Rodolfo R. Rodriquez, this can be achieved by inserting a precision-molded plastic float into the blood sample in the sample tube prior to centrifugation. The float has approximately the same density as the cells in the buffy coat region, and thus becomes suspended in that region after centrifugation. Since the outer diameter of the float is only slightly less than the inner diameter of the sample tube (typically by about 80 $\mu$m), the length of the buffy coat region will expand to make up for the significant reduction in the effective diameter of the tube that the buffy coat region can occupy due to the presence of the float. By this method, an expansion of the length of the buffy coat region by a factor of about 4 and 20 can be obtained. The cell counts calculated for the components of the buffy coat region will take into account the expansion factor attributable to the float.

Another technique that is used to enhance the accuracy of the layer thickness measurements is the introduction of fluorescent dyes (in the form of dried coatings) into the sample tube. When the blood sample is added to the sample tube, these dyes dissolve into the sample and cause the various blood cell layers to fluoresce at different optical wavelengths when they are excited by a suitable light source. As a result, the boundaries between the layers can be discerned more easily when the layer thickness are measured following centrifugation.

Typically, the centrifugation step and the layer thickness measurement step are carried out at different times and in different devices. That is, the centrifugation operation is first carried out to completion in a centrifuge, and the sample tube is then removed from the centrifuge and placed in a separate reading device so that the blood cell layer thickness can be measured. More recently, however, a technique has been developed in which the layer thickness are calculated using a dynamic or predictive method while centrifugation is taking place. This is advantageous not only in reducing the total amount of time required for a complete blood count to be obtained, but also in allowing the entire procedure to be carried out in a single device. Apparatus and methods for implementing this technique are disclosed in the aforementioned patents of Stephen C. Wardlaw entitled "Assembly for Rapid Measurement of Cell Layers", U.S. Pat. No. 5,889,584 and "Method for Rapid Measurement of Cell Layers", Ser. No. 08/814,535.

In order to allow the centrifugation and layer thickness steps to be carried out simultaneously, it is necessary to freeze the image of the sample tube as it is rotating at high speed on the centrifuge rotor. This can be accomplished by means of xenon flash lamp assembly that produces, via a lens and a bandpass filter, an intense excitation pulse of blue light energy (at approximately 470 nanometers) once per revolution of the centrifuge rotor. The pulse of blue light excites the dyes in the expanded buffy coat area of the sample tube, causing the dyes to fluoresce with light of a known wave length. The emitted fluorescent light resulting from the excitation flash is focused by a high-resolution lens onto a linear CCD array. The CCD array is located behind a bandpass filter which selects the specific wavelength of emitted light to be imaged onto the CCD.

The xenon flash lamp assembly is one of two illumination sources that are focused onto the sample tube while the centrifuged rotor is in motion. The other source is an array of light-emitting diodes (LEDs) which transmits red light through the sample tube for detection by the CCD array through a second band pass filter. The purpose of the transmitted light is to initially locate the beginning and end of the plastic float (which indicates the location of the expanded buffy coat area), and the full lines. Further details of the optical reading apparatus may be found in the aforementioned pending application of Michael R. Walters entitled "Inertial Tube Indexer", Ser. No. 09/032,931 and U.S. Pat. No. 6,120,429 and in the aforementioned U.S. Pat. No. 6,030,056 of Bradley S. Thomas entitled "Flash Tube Reflector with Arc Guide".

Since it is desirable to read the layers in the centrifuge blood sample while the centrifuged blood sample remains in the centrifuge, it is also desirable to insure that the readings are as accurate as possible. It is therefore necessary to accurately monitor the orientation of the rotor in which the blood sample is being centrifuged in relation to the optical reading device, so that the optical reading device will perform the readings at the exact times that the centrifuged blood sample is in the reading area. Since the rotor is spinning at several thousands of revolutions per minute, it is necessary to synchronize the reading perfectly with the rotation of the rotor so that the sample can be read without slowing down the rotation speed.

As described above, it is also desirable to rotate the sample tube about its longitudinal axis, so that readings can be taken at different locations about the circumference of the blood tube, thus providing a more accurate measurement of the lengths of the blood component layers in the centrifuged blood sample. Details of an indexing apparatus for performing this function may be found in the aforementioned copending application of Michael R. Walters entitled "Inertial Tube Indexer", Ser. No. 09/032,931. Additionally, it is also desirable to be capable of reading different portions of the blood sample at different times. Furthermore, because the readings are based on light being transmitted through the centrifuged sample and light that is emitted from the centrifuged sample in response to excitation light irradiated onto the centrifuge sample, it is desirable to prevent light of unwanted wavelengths from being detected to improve the readings being taken by the optical detector.

Accordingly, a continuing need exists for an apparatus which is capable of centrifuging a blood sample stored in a sample tube, and taking accurate measurements of the component layers of the centrifuged blood sample while the sample tube remains in the centrifuge device and continues to be rotated by the rotor of the centrifuge device.

SUMMARY OF THE INVENTION

An object of the present invention is to provide a centrifuge device that is capable of centrifuging a blood sample contained in a sample tube, and accurately reading the component layers that are formed in the blood sample as a result of the centrifugation without removing the sample tube from the centrifuge device.

Another object of the invention is to provide a centrifuge device having a component layer reader which is capable of scanning the centrifuged blood sample to read different portions of the centrifuge blood sample at different times.

A further object of the invention is to provide a centrifuge device which is capable of monitoring the orientation of the rotor in which the blood tube containing the blood sample being centrifuged is loaded, to control the reading of the centrifuge blood sample and the loading and unloading of the blood sample tube.

Another object of the invention is to provide a movable optical reader, for use with the centrifuge device, which is capable of reading the component layers in a centrifuge blood sample while the rotor of the centrifuge device is continuing to rotate the centrifuged blood sample.

A still further object of the invention is to provide a movable optical reader as described above, which includes an excitation light source that irradiates light onto the centrifuge blood sample, and which further includes a reading device which receives light emitted by the centrifuge blood sample in response to the excitation light, to read the component layers of the centrifuged blood sample, and which further includes a filter array having a plurality of filters which are selectable to substantially prevent light having certain wavelengths from being received by the reading device.

These and other objects of the invention are substantially achieved by providing an optical reader assembly, adaptable for use in a centrifuge device which operates to centrifuge a fluid sample, such as a blood sample, comprising a carriage assembly which is adaptable to movably support an optical reader that is adaptable to receive light emitted from the blood sample. The optical reader assembly further includes a driving mechanism which is adaptable to move the optical reader in the carriage assembly when the optical reader is being adapted to receive the emitted light from the blood sample. The driving mechanism can move the optical reader incrementally so that the optical reader can receive light emitted from different portions of the blood sample at different times. The optical reader assembly can further comprise an excitation light source which is adaptable to emit excitation light toward the blood sample to cause the sample to emit the emitted light, and a filter array having a plurality of filters which are selectable to prevent light having certain wavelengths from being received by the optical reader when the optical reader is reading the blood sample. The optical reader assembly also can include a transmission light source which is adaptable to emit transmission light towards the fluid sample, and the optical reader can be further adaptable to receive a portion of the transmission light passing through the blood sample.

The above objects of the invention, as well as other objects, are further substantially achieved by providing a centrifuge device comprising a rotor that is adaptable to rotate a container which contains a blood sample to separate the blood sample into a plurality of component layers in the container, and a detector device that is adaptable to detect the component layers in the container while the rotor is rotating the container. The detector device can include the features of the optical reader assembly discussed above. The centrifuge device further can include a detector which detects the orientation of the rotor, to thus control the detector device to control the reading of the blood sample, as well as to position the rotor for loading and unloading of the blood sample container. The centrifuge device can also include detectors which detect whether the container has been loaded in the rotor, and whether the container is properly secured in the rotor.

BRIEF DESCRIPTION OF THE DRAWINGS

These and other objects of the invention will be more readily appreciated from the following detailed description when read in conjunction with the accompanying drawings, in which:

FIGS. 29A–29C are schematics showing the relationships between the flash tube, arc guide, CCD array, filters, LED bar and carrier tube when the rotor assembly positions the carrier tube and the CPU energizes the flash tube to perform open fluorescence readings, green emission readings or red emission readings;

Throughout the drawings, like reference numerals will be understood to refer to like parts and components.

DETAILED DESCRIPTION OF THE PREFERRED EMBODIMENTS

Figure 1:
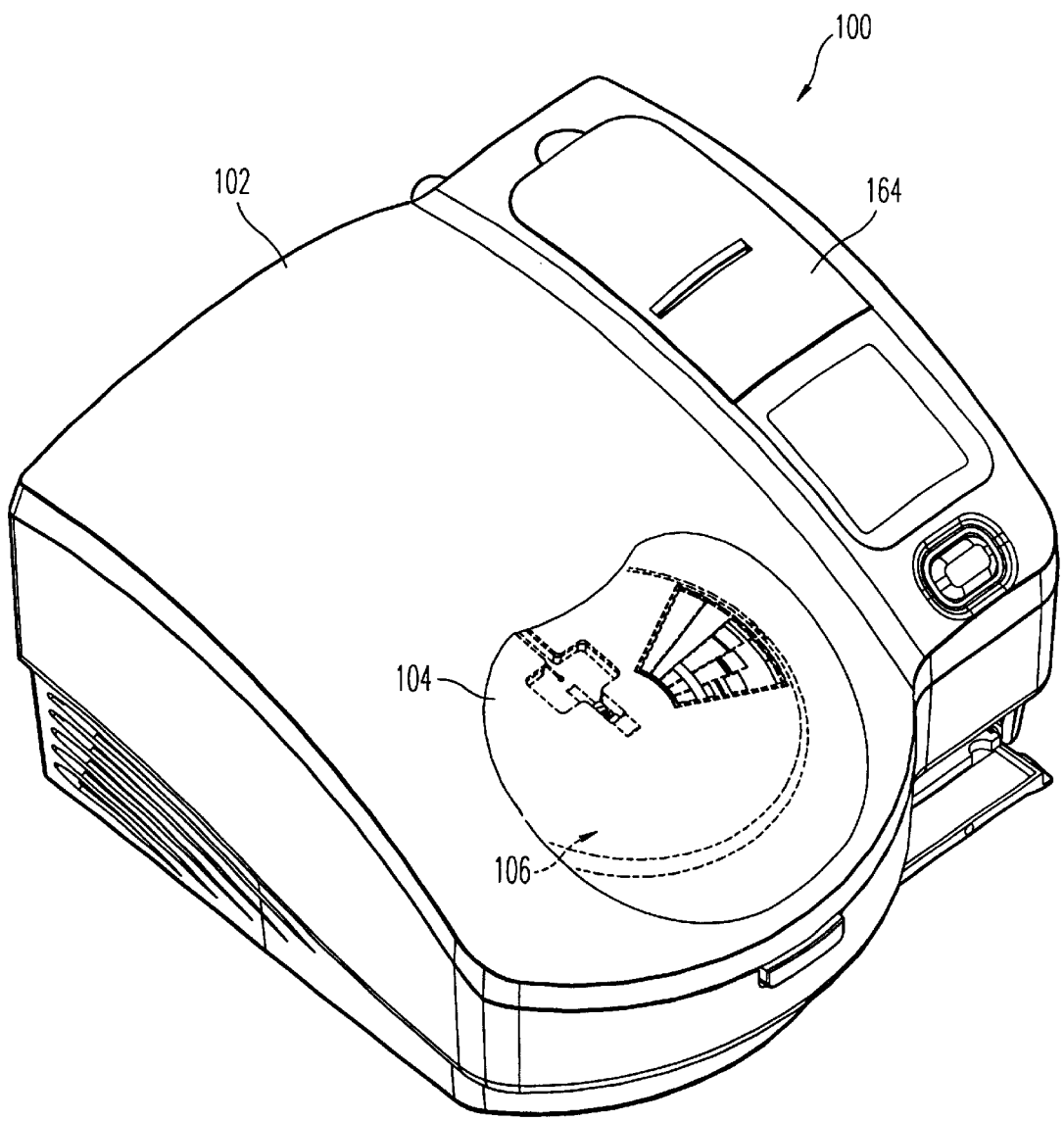
FIG. 1 is a perspective view of a centrifuge device in which the indexing apparatus according to the present invention can be used.
Figure 2:
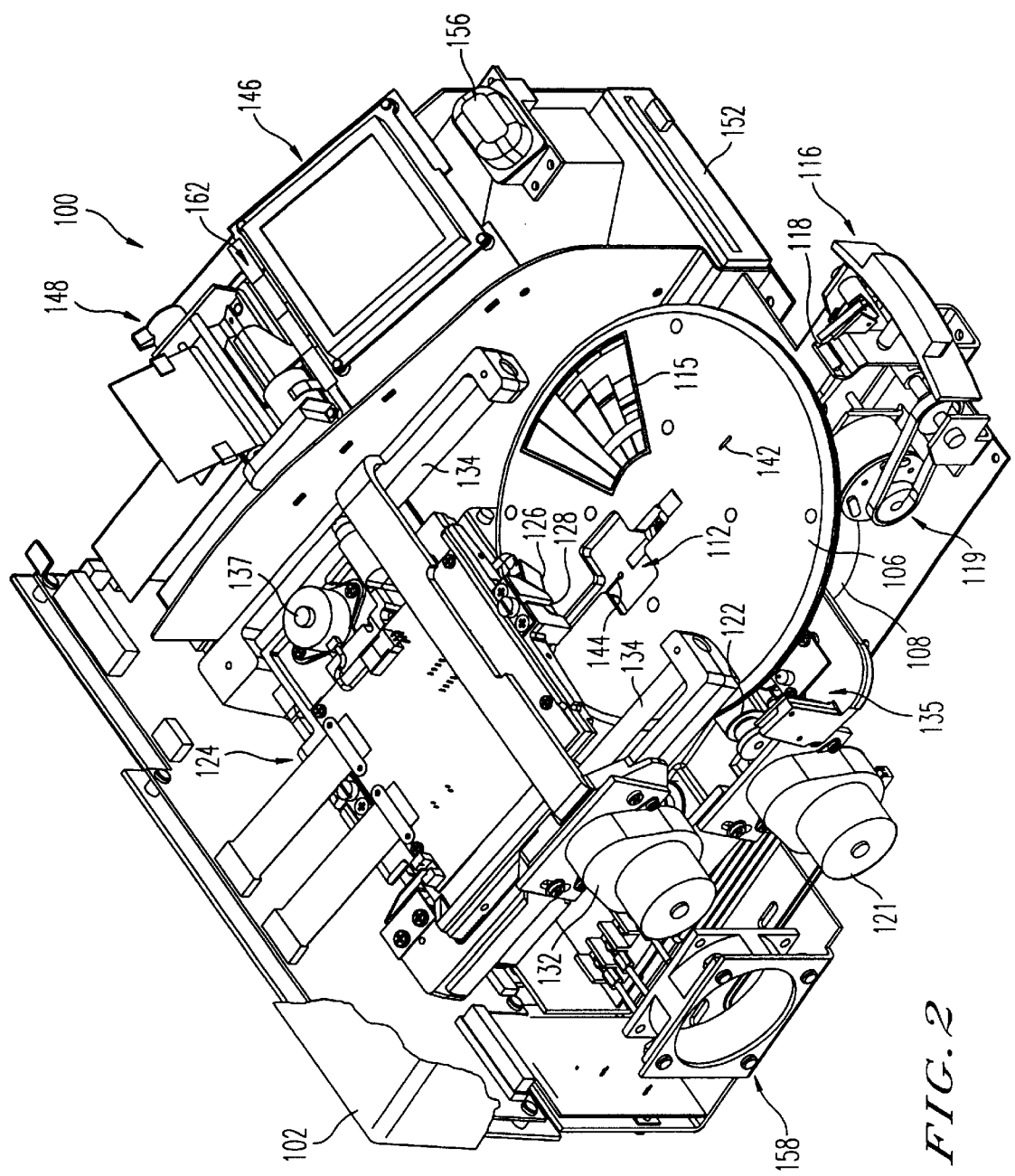
FIG. 2 is a detailed perspective view of the centrifuge device shown in FIG. 1, with the cover being removed to expose the internal components of the device.
Figure 3:
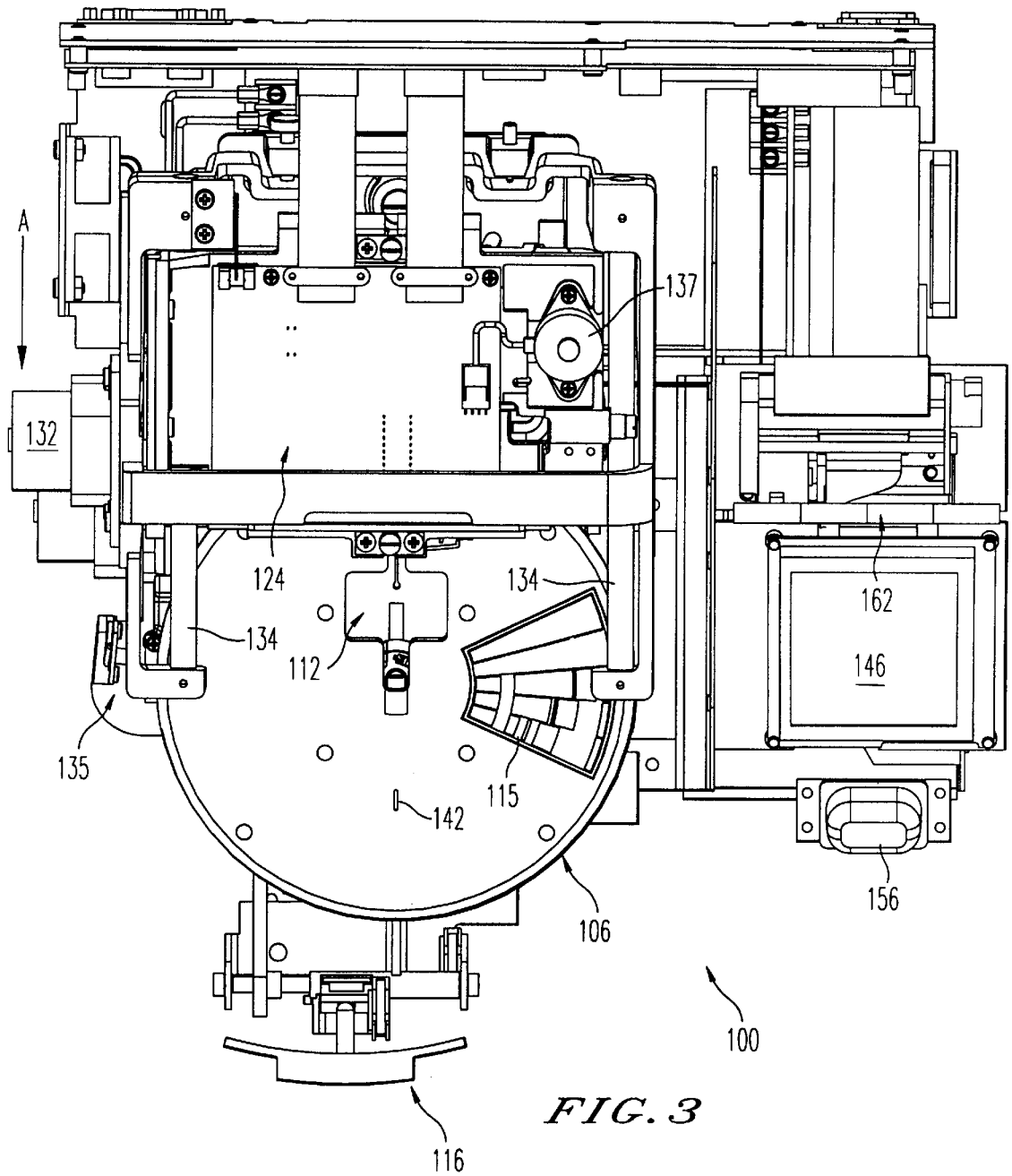
FIG. 3 is a top plan view of the centrifuge device shown in FIG. 2.
Figure 4:
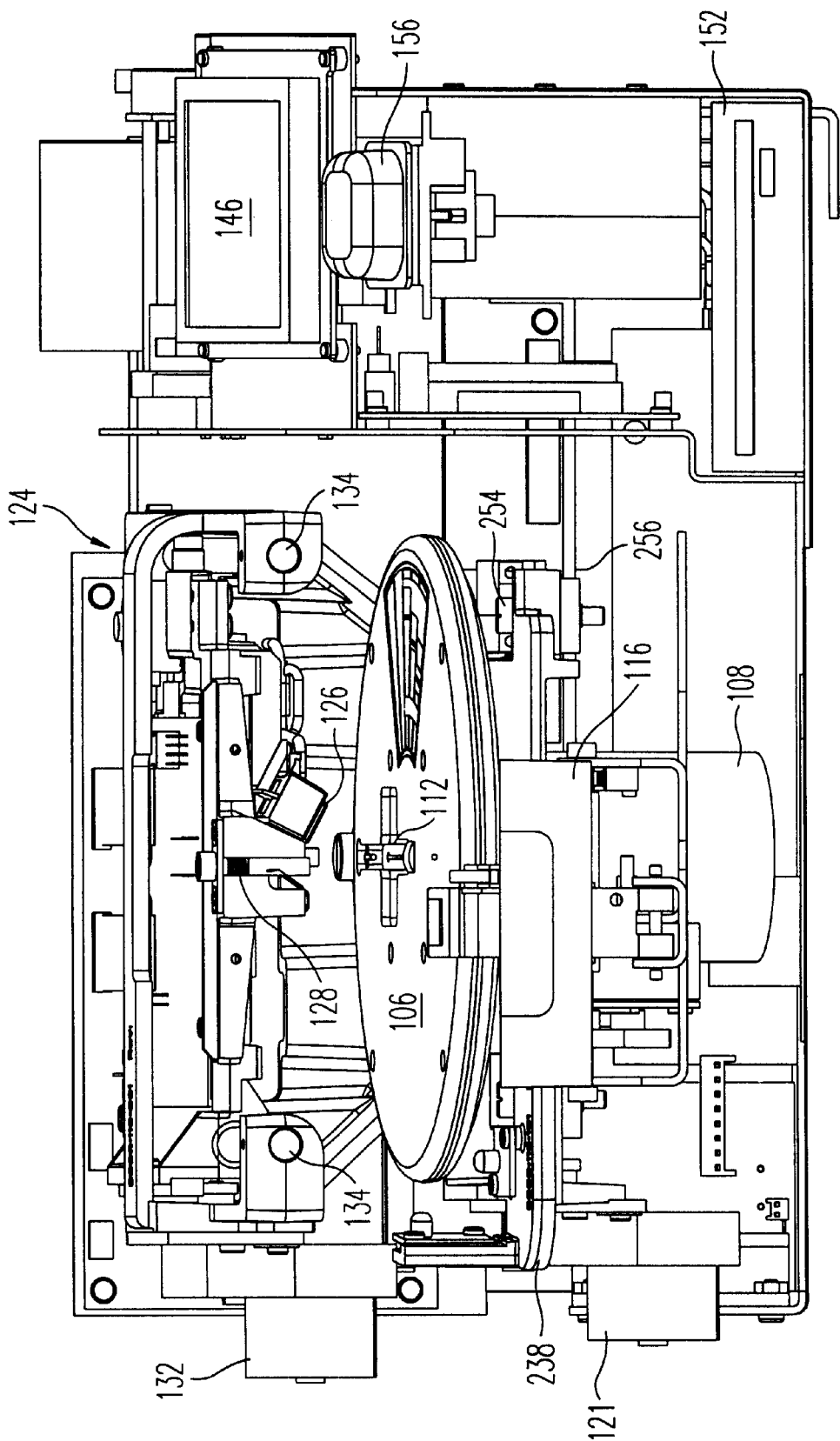
FIG. 4 is a front plan view of the centrifuge device shown in FIG. 2.

A centrifuge device 100 according to an embodiment of the present invention is shown in FIGS. 1–4. FIG. 1 illustrates the centrifuge device 100 having a cover 102 and a lid 104 which is positioned in an open position. The centrifuge device 100 is a relatively compact device having a weight of less than about 20 pounds, a width of less than about 15 inches, a height of less than about 9 inches, and a depth of less than about 15 inches. However, the size and weight of the centrifuge device 100 can be varied in accordance with desired design modifications. The cover 102 and lid 104 can be made of a hard plastic or any other suitable material. As illustrated in FIGS. 2–4, the cover 102 of the centrifuge device 100 has been cut away to expose the internal components of the centrifuge device 100.

Figure 5:
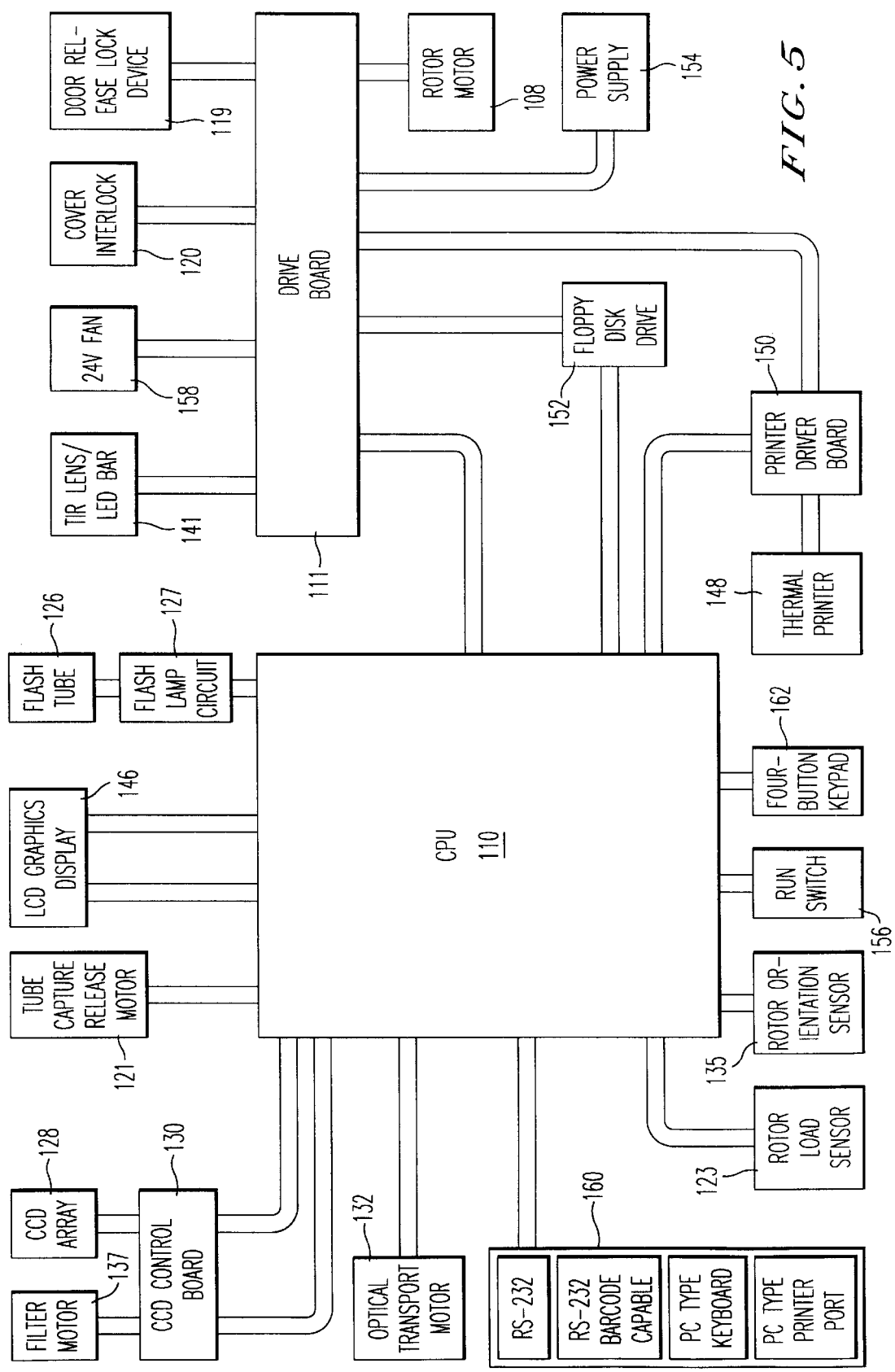
FIG. 5 is a block diagram showing some of the electrical components of the centrifuge device shown in FIGS. 1 and 2.
Figure 6:
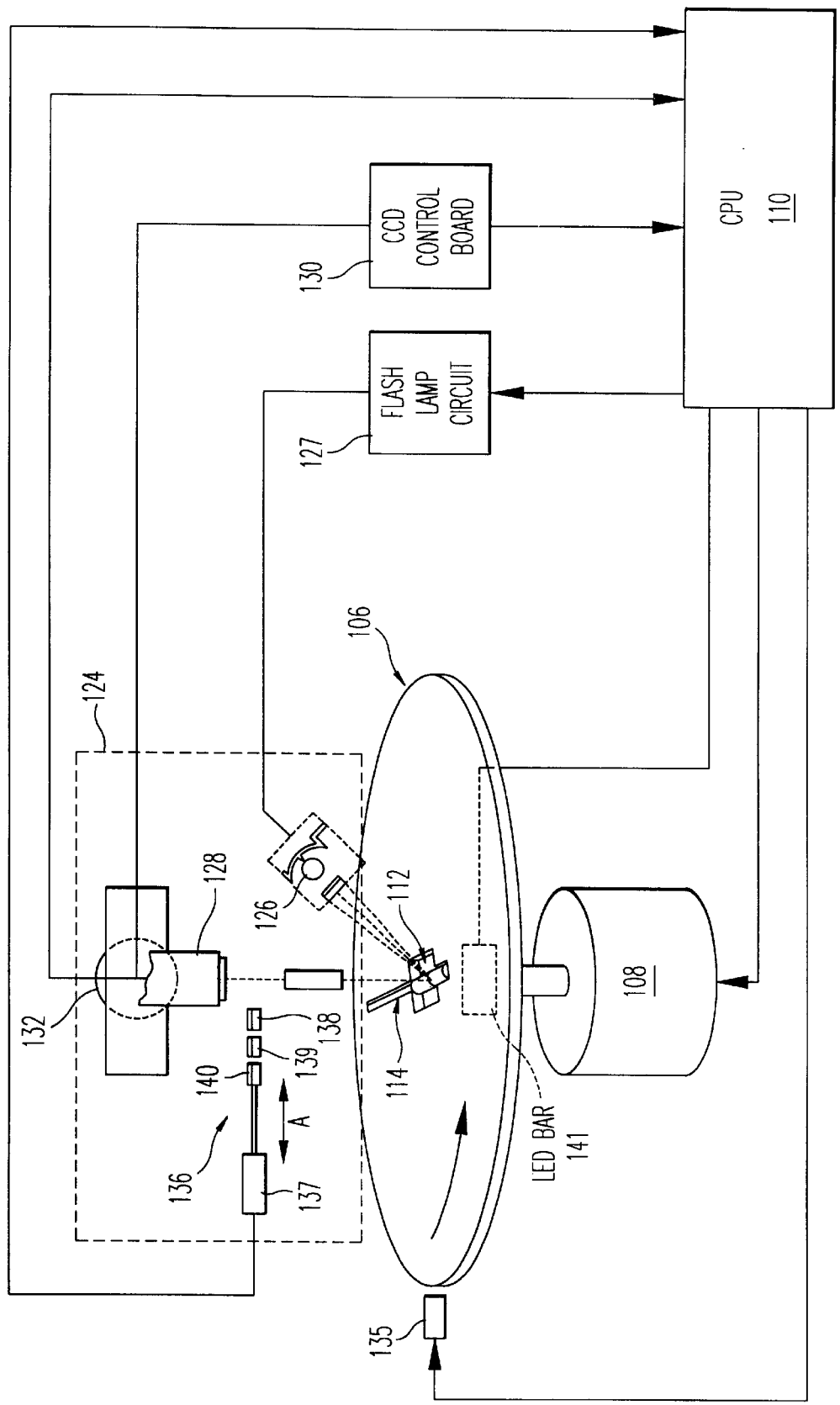
FIG. 6 is a schematic illustrating an example of the relationship between the rotor and optical reading device and some of their associated electrical and mechanical components of the centrifuge device shown in FIGS. 1–4.

As shown in FIGS. 2–4, the block diagram of FIG. 5, and the schematic of FIG. 6, the centrifuge device 100 includes a rotor assembly 106 that is driven by a rotor motor 108 as controlled by a CPU 110 via a drive board 111. The rotor assembly 108 is typically about 6.9 inches in diameter (but can have any practical diameter), and can be made of any suitable material such as a molded composite material, plastic, metal or the like. The rotor motor 108 is a direct drive brushless DC motor and is mounted on vibration isolation mounts (not shown) to reduce acoustic noise and vibration effects on the optics.

The CPU 110 in this example is a 186 processor running at 40 Mhz. The CPU 110 controls the rotor motor 108 via drive board 111 to rotate within a range of about 1,000 to 12,000 r.p.m. The CPU 110 can also control the rotor motor 108 to stop the rotor assembly 106 in a maximum of about 10 seconds. The CPU 110 also includes a "watchdog timer" which is re-initialized every few seconds to keep the rotor motor 108 running. This "watchdog timer" feature creates a safety shutdown in the event that the CPU 110 fails.

The rotor motor assembly 106 is housed in the centrifuge device 100 such that the interior of the centrifuge device 100 is formed to contain the rotor assembly 106 in an explosion containment chamber, which will contain all fragments in case of rotor assembly failure at full rotation speed. Neither the centrifuge device 100 as a whole, or any part from it, can move outside of a 30 cm safety zone surrounding the centrifuge device 100 as a result of rotor assembly failure.

As described in more detail below, the rotor assembly 106 includes a carrier tube accommodating recess 112 having an indexing mechanism 113 located therein, the construction and operation of which can be found in the aforementioned copending application of Michael R. Walters et al. entitled "Inertial Tube Indexer and Method for Using the Same", Ser. No. 09/032,931. A carrier tube 114 as described in the aforementioned U.S. Pat. No. 6,080,366 of Edward G. King et al. entitled "Disposable Blood Tube Holder and Method for Using the Same", can be loaded into the carrier tube accommodating recess 112 and engaged by the indexing mechanism 113 as described below. The rotor assembly 106 further includes a calibration label 115 which is used to calibrate the centrifuge device 100 as described in more detail below.

The centrifuge device 100 further includes a door release and lock mechanism 116, which includes a door lock 118 that is mechanically operable, and also controllable by a door release/lock drive 119, such as a motor or solenoid which is controlled by CPU 110 via the drive board 111. As discussed in more detail below, the door release and lock mechanism 118 is operated by a user to release the door 104, and thus allow the door 104 to be positioned in the open position as shown in FIG. 1 to provide access to the rotor assembly 106 and, in particular, the carrier tube accommodating recess 112 for insertion and removal of a carrier tube 114. The door release/lock device 119 is also controlled by the CPU 110 to control the door lock 118 to maintain the door 104 in the closed and locked position when the rotor assembly 106 is being driven by the rotor motor 108. A cover interlock sensor 120 senses when the door 104 is locked, and provides a signal to the CPU 110 to this effect via the drive board 111.

As further shown, the centrifuge device 100 includes a tube capture and release motor 121 that is controlled by the CPU 110. As discussed in more detail below, the CPU 110 controls the tube capture and release motor 122 to drive an engaging mechanism 122 to engage a tube holding assembly of the rotor assembly 106 to allow a carrier tube 114 to be loaded into and removed from the carrier tube accommodating recess 112, and to release the tube holding assembly so that the tube holding assembly secures the carrier tube 114 in the carrier tube accommodating recess 112. A rotor loaded sensor 123, which can be an optical sensor, detects when the engaging mechanism 122 has returned to its home position after engaging the tube holding assembly and provides a signal to CPU 110. The CPU 110 interprets this signal as an indication that a carrier tube 114 has been loaded into the rotor assembly 106.

As further illustrated, the centrifuge device 100 further includes an optical carriage assembly 124 that includes a flash tube 126 that is energized by a flash lamp circuit 127 as controlled by the CPU 110. The optical carriage assembly further includes a CCD array 128 which is described in more detail below. The CCD array 128 is controlled by a CCD control board 130 that is controlled by CPU 110 to operate in cooperation with flash tube 126, so that when flash tube 126 is driven to emit light towards the carrier tube 114 loaded in the rotor 106, the CCD array 128 is controlled to read light that is illuminated by the contents (e.g., a blood sample) of a capillary tube contained in the carrier tube 114 in response to the light emitted by the flash tube 126. These and other features of the flash tube 126 and CCD array 128, as well as the operation of the carriage assembly 124 as a whole, are described in more detail below, and in the aforementioned U.S. Pat. No. 6,03086, Ser. No. 09/032,935.

The optical carriage assembly 124 further includes an optics transport motor 132 which controls the movement of the optical carriage assembly 124 and, in particular, the movement of the CCD array 128, along guide rails 134 in a direction radial of the rotor assembly 106. The optics transport motor 132 is controlled by CPU 110 to move the optical carriage array 124 in this manner so that the CCD array 128 can read the entire sample in the capillary tube contained in the carrier tube 114.

The centrifuge device 100 includes a rotor assembly orientation sensor 135 which, as described in more detail below, senses when the rotor assembly 106 is oriented such that the carrier tube 114 is positioned below the CCD array 128, and provides a signal to CPU 110. When the CPU 110 receives the signal from the rotor assembly orientation sensor 135, the CPU 110 determines the instant at which the flash tube 126 should be energized. Specifically, the CPU 110 creates a digital delay between the time it receives the signal from the rotor assembly orientation sensor 135 and the time at which the flash tube 126 is energized. This delay time varies to correct for variations in the speed of rotation of the rotor assembly 106, and for mechanical tolerances. When the CPU 110 determines that the flash tube 126 should be energized, the CPU 110 controls the flash tube circuit 127 to drive the flash tube 126, and controls the CCD control board 130 to control the CCD array 128 to read the light emitted from the sample in the capillary tube.

The optical carriage assembly 124 further includes a filter rack 136 which includes a red emission filter 138, a green emission filter 139, and a blue blocking filter 140. The filter rack 136 is driven by filter motor 137 to move in a direction indicated by Arrow A in FIG. 4, so that each of the individual filters of the filter rack 136 can be positioned in front of the CCD array 128 as desired as described in more detail below. Each filter 138, 139, 141 in the filter rack 136 is capable of filtering out light having particular wavelengths from the light being emitted by the sample in carrier tube 114, while allowing light of a desired wavelength to pass to the CCD array 128.

Additionally, the centrifuge device 100 includes an LED bar 141 which is disposed below the motor assembly 106 and is controlled by CPU 110 via the drive board 111 to emit light in the direction of rotor assembly 106. This light can pass through slits 142 and 144 in the rotor assembly 106, and be detected by CCD array 128 as the rotor assembly 106 rotates, to ascertain the presence and absence of a carrier tube 114 and the correct positioning of the carrier tube 114 in the carrier tube accommodating recess 112 as described in more detail below.

The centrifuge device 100 also includes an LCD graphics display 146 that is controlled by the CPU 110 to display, for example, information pertaining to the operation of the centrifuge device 100, and information pertaining to the readings of the sample in the capillary tube contained in the carrier tube 114 as taken by the centrifuge device 100. The centrifuge device 100 further includes a thermal printer 148 that uses a 2.25 inch to 2.75 inch wide tape and is controlled by the CPU 110 via a printer driver board 150 to print out information pertaining to, for example, readings of the centrifuged sample in the capillary tube as taken by the centrifuge device 100.

The centrifuge device 100 also includes a floppy disk drive 152, such as a 3.5 inch 1.44 Mb floppy drive, which can receive a standard floppy disk to which data, such as readings of the centrifuged sample, can be written by the CPU 110, or from which data, such as patient data, control information or the like can be read by the CPU 110.

Also, software updates can be provided to the CPU 110 by a floppy disk loaded into the floppy disk drive 152. Each time power is turned on for the centrifuge device 100, the CPU 110 checks the floppy disk drive 152. If the floppy disk drive 152 contains a software distribution floppy disk on which is stored a newer version of the software, the newer version of the software is automatically updated by the CPU 110 and hence, the software which controls the centrifuge device 100 is automatically upgraded.

Additionally, the centrifuge device includes a power supply 154 which can, for instance, be plugged into an AC outlet to provide power to the centrifuge device 100. The power supply 154 is designed for universal use with an autoranging A.C. input allowing it to operate over a continuous means voltage range of 90 VAC to 265 VAC and at 47 Hz to 63 Hz. The guaranteed minimum starting voltage should be 80 VAC, and the power supply 154 should be capable of brief periods of operation at up to 300 VAC. Steady state power consumption should not exceed 15.0 watts, and peak power during rotor assembly acceleration should not exceed 250 watts. The centrifuge device 100 further includes a run/stop button 156 which controls the centrifuge device 100 to begin centrifuging the sample, a fan 158 which can be controlled by the CPU 110 via the drive board 111 to cool the internal components of the centrifuge device 100, and a plurality of interface ports 160 which are capable of coupling to the CPU 110 various types of interface devices, such as a bar code reader, a PC type keyboard, a PC type printer, a RS-232 module, and so on. The centrifuge device 100 also includes a four button key pad 162 which enables an operator to enter information to control the operation of the centrifuge device 100. The key pad 162 can be located, for example, underneath a lid 164 which also provides access to the thermal printer 148, so that printing paper can be replaced, ink cartridges can be replaced, and so on.

Figure 7:
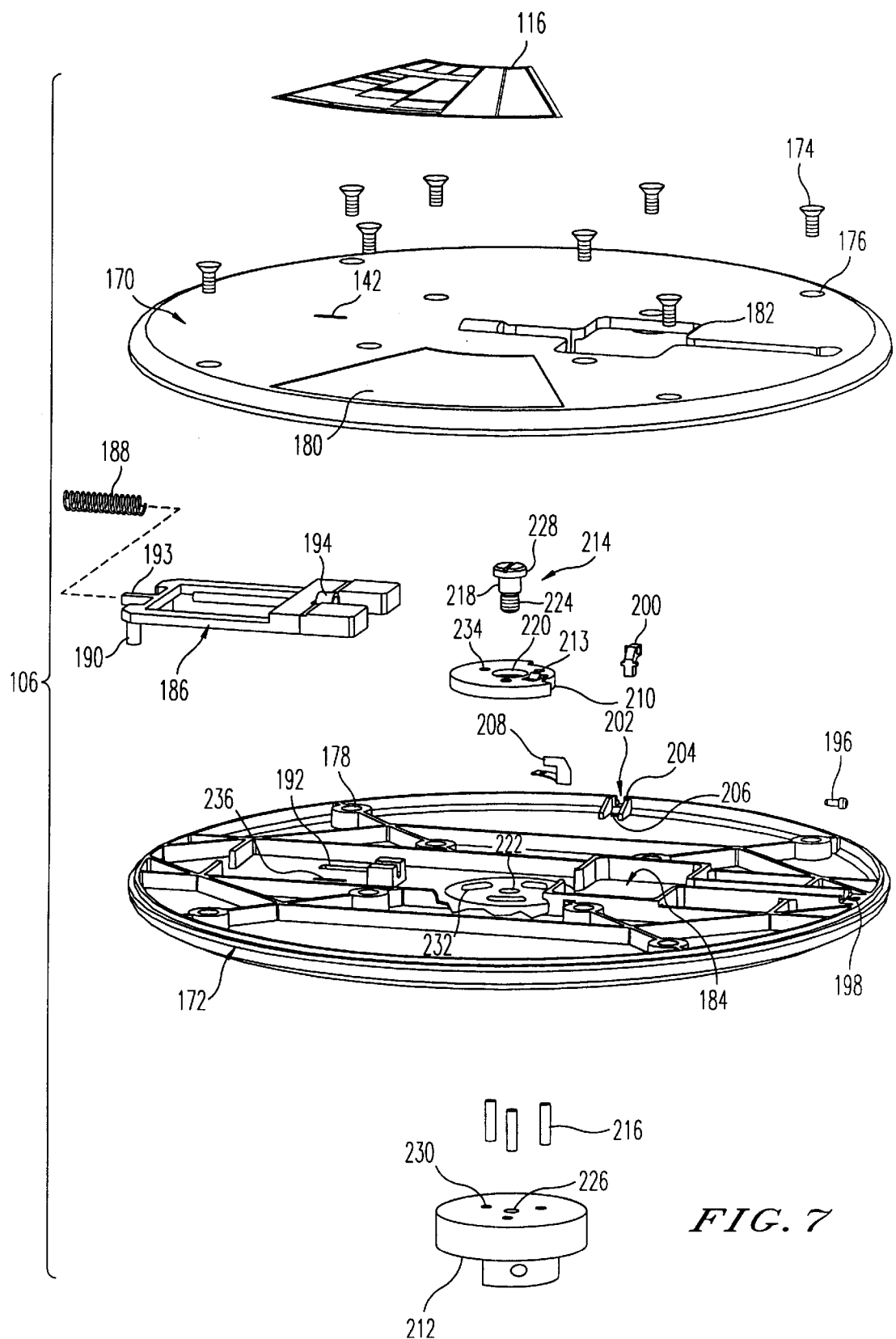
FIG. 7 is a detailed exploded perspective view of the rotor assembly of the centrifuge device shown in FIGS. 1–4.

The rotor assembly 106 will now be described in more detail with respect to FIG. 7. As shown in FIG. 7, the rotor assembly includes a rotor top 170 and a rotor bottom 172 that are coupled together by screws 174 which pass through corresponding openings 176 in the rotor top 170 and are received into corresponding screw receiving holes 178 in rotor bottom 172. The rotor top 170 and rotor bottom 172 can be made of any suitable material, such as metal, plastic, or preferably, a molded, composite material. Also, the rotor top 170 and rotor bottom 172 can alternately be snap-fit together, bonded, fit together by any other suitable fastener.

The calibration label 116 attaches to the label section 180 of rotor top 170. Also, rotor top 170 includes an opening 182 which, in cooperation with the cavity arrangement 184 in rotor bottom 172, forms the carrier tube accommodating recess 112.

The rotor assembly 106 further includes a carrier tube holder assembly 186 that is biased by a compression spring 188 as is described in more detail below. The carrier tube holder assembly 186 includes legs 190 which pass through corresponding slotted openings 192 in the rotor bottom 172, and a projection 193 which is described in more detail below. The carrier tube holder assembly 186 further includes a cup 194 which, as described in more detail below, receives an end of the carrier tube 114 when the carrier tube 114 is received in the carrier tube accommodating recess 112 of the rotor assembly 106.

The rotor assembly 106 further includes an engaging pin 196 which is mounted in pin receiving recess 198 in the rotor bottom 172 so that the front end of the pin 196 projects into the carrier tube accommodating recess 112 of the rotor assembly 106 and thus engages an end of the carrier tube 114 that is inserted in the carrier tube accommodating recess 112 as will be described in more detail below. The rotor assembly also includes a light pipe 200 that is inserted into light pipe receiving opening 202 in the rotor bottom 172. As described in more detail below, the light pipe 200 is configured so that light traveling in a direction radial to the rotor assembly 106 which enters the light pipe 200 through a light pipe side opening 204 is redirected by the light pipe 200 to exit the bottom of the rotor assembly 106 through light pipe bottom opening 206 in the rotor bottom 172.

The rotor assembly 106 further includes a pawl 208 that is secured to the rotor bottom 172 by, for example, heat staking or in any other suitable manner. The significance of pawl 208 is described in the aforementioned copending application of Michael R. Walters entitled "Inertial Tube Indexer", Ser. No 09/032,931.

The rotor assembly 106 also includes an index hub assembly 210 that is coupled to a rotor hub assembly 212 by a screw 214 and limit pins 216. The index hub assembly 210 has a cut-out portion 213 to accommodate pawl 208. A shaft portion 218 of the screw 214 passes through opening 220 in the index hub assembly 210, and through a central opening 222 in the rotor bottom 172, and a threaded portion 224 of the shaft portion 218 screws into opening 226 in motor hub 212. The diameter of the head 226 of the screw 214 is greater than the diameter of opening 218 in the index hub assembly 210 and thus, the screw 214 secures the index hub assembly 218, rotor bottom 172 and motor hub 212 together. Since the diameter of central opening 222 in the rotor bottom 172 is greater than the diameter of shaft portion 218 of the screw 214, the index hub 210 and motor hub 212 are rotatably coupled to the rotor bottom 172. Further details concerning the index hub 210, and the significance of this rotatable connection can be found in the aforementioned copending application of Michael R. Walters et al. entitled "Inertial Tube Indexer", Ser. No. 09/032,931.

Figure 8:
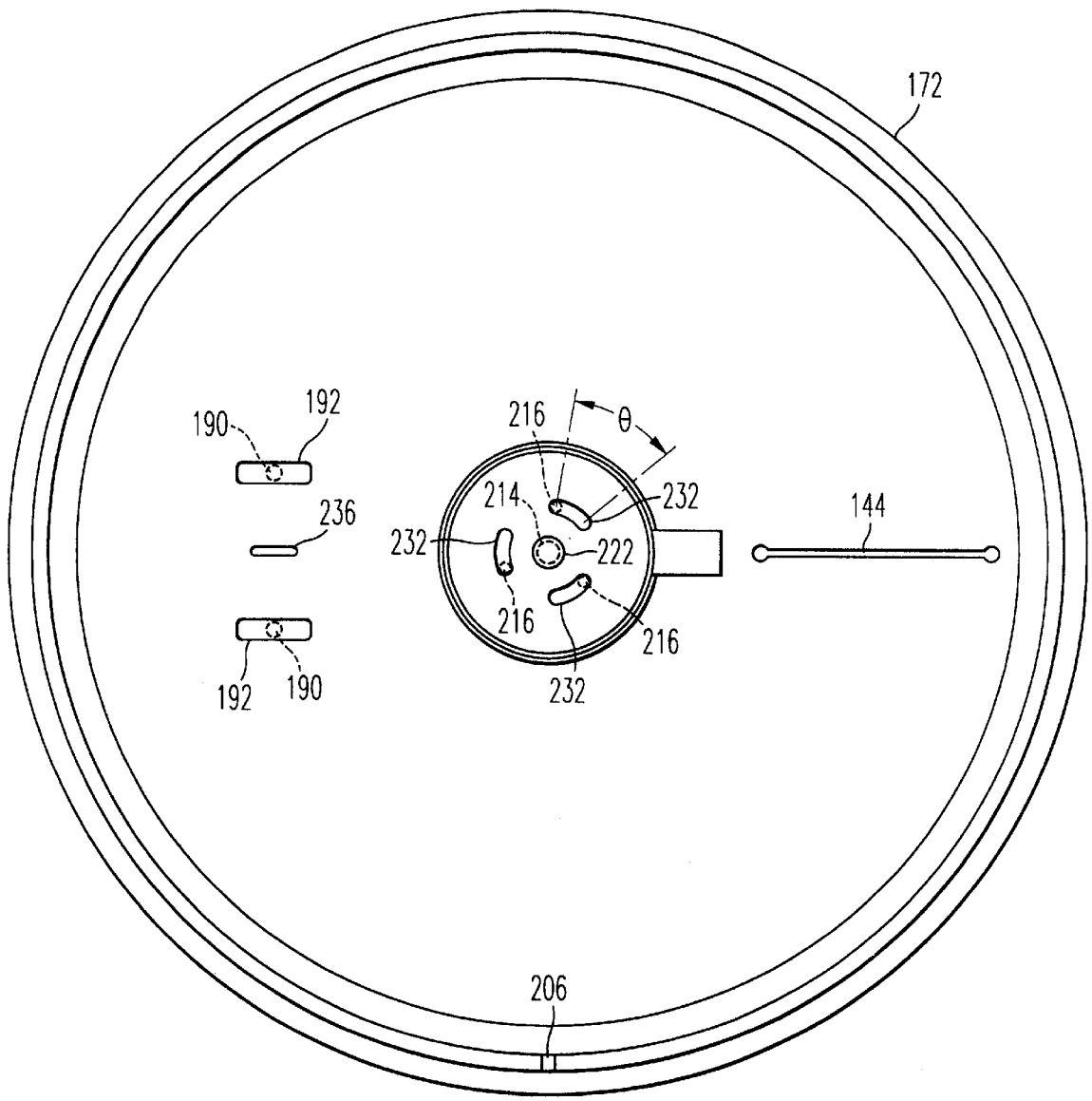
FIG. 8 is a bottom plan view of the rotor shown in FIG. 7.

As further illustrated, limit pins 216 are received and secured in respective openings 230 in the motor hub 212, and also pass through corresponding arcuate slots 232 in the rotor bottom 172 and are received and secured in corresponding openings 234 in the index hub assembly 210. As shown in FIG. 8, which is a plan bottom view of the rotor bottom 172 with the limit pins 216 and screw 214 shown in phantom, the arcuate slots 232 in the rotor bottom 172 limit the relative rotation of the index hub assembly 210 and motor hub assembly 212 with respect to the rotor bottom 172 to an angle θ. FIG. 8 also illustrates the slotted openings 192 with the legs 190 of the carrier tube holder assembly 186 shown in phantom, the light pipe bottom opening 206, the slit 144 (see FIG. 2), and a slit 236 which substantially aligns with slit 142 in the rotor top 170.

Figure 9:
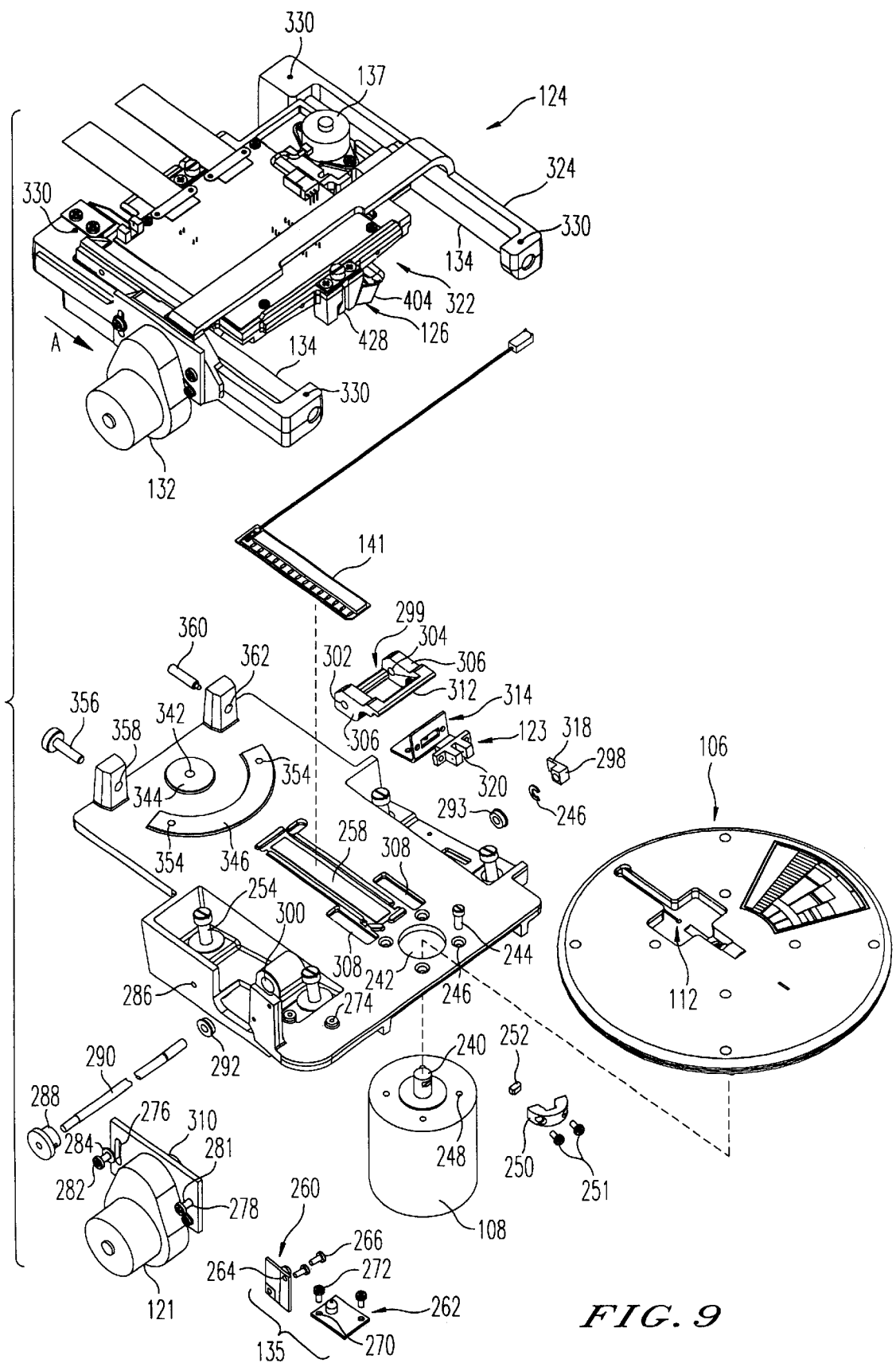
FIG. 9 is an exploded perspective view showing the relationship between the rotor assembly, rotor motor optical carriage assembly, tube capture and release motor and associated engaging mechanism, and LED bar of the centrifuge device shown in FIGS. 1 and 2.
Figure 10:
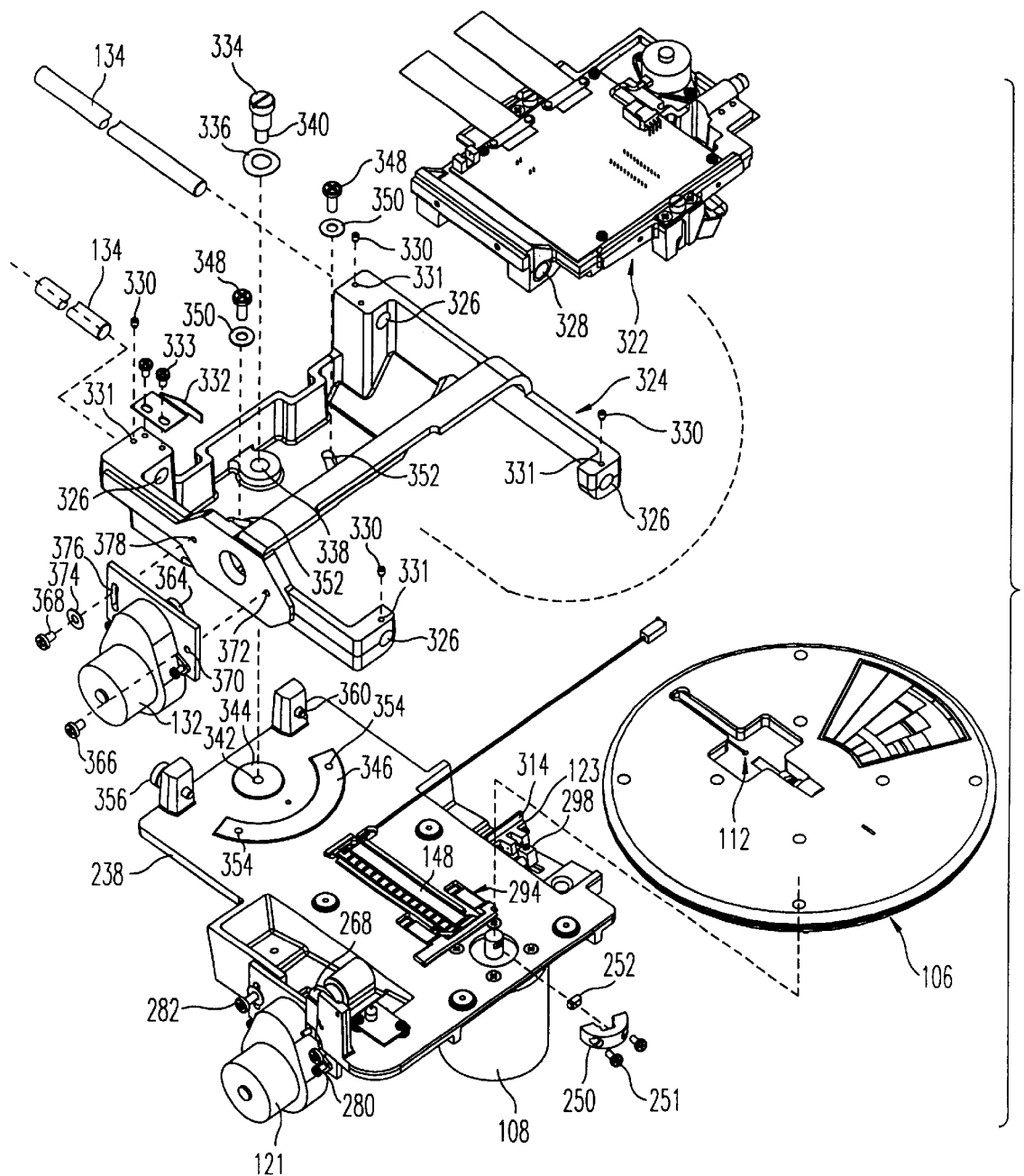
FIG. 10 is an exploded perspective view of the optical carriage assembly shown in FIG. 9.

FIGS. 9 and 10 are exploded perspective views illustrating the relationship between, among other things, the optical carriage assembly 124, rotor assembly 106, rotor motor 108, tube capture and release motor 121 and the engaging mechanism 122, and the LED bar 141.

As illustrated, the rotor motor 108 is secured to a frame portion 238 of the centrifuge device 100, such that the drive shaft 240 of the rotor motor 108 passes through an opening 242 in the frame portion 238. The rotor motor 108 is secured to the frame portion 238 by fastening members 244, such as screws, pins, rivets, or the like, which pass through corresponding openings 246 in the frame portion 238 and are received into corresponding openings 248 in the rotor motor 108. The rotor assembly 106 is positioned over the top of the frame portion 238, and the rotor hub assembly 212 (see FIG. 7) of the rotor assembly 106 is coupled to the drive shaft 240 of the rotor by a clamp 250, screw 251 and key 252 clamping arrangement, such that the rotor hub assembly 212 rotates essentially in unison with the drive shaft 240 of the rotor motor 108. The frame portion 238 is secured into the centrifuge device 100 by bolts 254 which are received into mounting holes (not shown) in another frame portion 256 (see FIG. 4) of the centrifuge device 100.

As further illustrated, the LED bar 141 is mounted in an opening 258 of the frame portion 238, so that the LED bar 141 is positioned below the rotor bottom 172 (see FIG. 7) of the rotor assembly 106. In this example, the LED bar 141 includes a row of sixteen 660 nm LED's, which are bare die on ceramic substrate construction and arranged to emit light in the direction toward the rotor bottom 172. The 16 LEDs are covered by a TIR transmission lens having an integral 20°×80° light shaping diffuser. The hybrid ceramic circuit board includes printed current limiting resistors that are individually laser trimmed to produce an intensity gradient from 100% at the rim of the rotor assembly 106 to 40% toward the center of the rotor assembly 106. This compensates for the variation in exposure time due to an increase in linear velocity with the radius of the rotor assembly 106.

As further illustrated, the rotor assembly orientation sensor 135 includes an emitter assembly 260 which, in this example, includes a light emitting diode mounted to a printed circuit board, and a detector assembly 262 which, in this example, includes a photodiode or phototransistor mounted to a printed circuit board. The printed circuit board of the emitter assembly 260 includes openings 264. Fastening members 266, which are screws (but can be any suitable type of fastening members such as pins, rivets, or the like), pass through corresponding openings 264 in the printed circuit board and are received into corresponding openings 268 in the frame portion 238 to mount the emitter assembly 260 to the frame portion 238 as shown. Similarly, the printed circuit board of detector assembly 262 includes openings 270 which receive corresponding fastening members 272 which, in this example, are screws (but can be any suitable fastening members such as pins, rivets, or the like). The fastening members 272 are received into corresponding openings 274 in the frame portion 238 to thus couple the detector assembly 262 to the frame portion 238 as shown.

As further shown, the tube capture and release motor 121 includes a slotted opening 276 and an opening 278. A fastening member 280, such as a screw, is received into opening 278 and is further received into an opening (not shown) in the frame portion 238 to mount the tube capture and release motor 121 to the frame portion 238. A fastening member 282, such as a screw, is assembled with a washer 284 and passes through slotted opening 276 in the tube capture and release motor 121, and is received into an opening 286 in the frame portion 238 to further secure the tube capture and release motor 121 to the frame portion 238. Before the fastening members 280 and 282 are fully tightened in their respective openings in the frame portion 238, the slotted opening 276 enables the position of the tube capture and release motor 121 to be adjusted by allowing the tube capture and release motor 121 to be moved relative to fastening member 282.

As further illustrated, the engaging mechanism 122 includes a gear 288, a shaft 290, bearings 292, and engaging member 294, a retainer ring 296 and a flag 298. The gear 288 is coupled to the shaft 290 which passes through an opening in bearing 292 and into an opening 300 in the frame portion 238. After passing through opening 300, the shaft 290 passes through openings 302 and 304 of the engaging member 294, which has been positioned such that its legs 306 pass through respective openings 308 in the frame portion 238. The shaft 290 then passes out of another opening (not shown) in frame portion 238 opposite to opening 300. The end of the shaft 290 opposite to that at which gear 288 is attached is assembled to bearing 293, retainer ring 296 and flag 298. Hence, the retainer ring 296 retains the shaft 290 in the openings in the frame portion 238. The engaging member 294 is coupled to the shaft 290 so that the engaging member 294 rotates essentially in unison with the shaft 290.

That is, as described in more detail below, the gear 288 engages with a gear 310 that is driven by the tube capture and release motor 121, so that as the gear 310 is rotated by the tube capture and release motor 121, the gear 306 rotates the gear 288 and thus, rotates the shaft 290 and engaging member 294. As illustrated, the legs 306 of engaging member 294 pass through corresponding openings 308 in the frame portion 238 so that the engaging portion 312 of the engaging member 294 is capable of contacting the legs 190 of the carrier tube holder assembly 186 is as described in more detail below.

As further illustrated, a sensor bracket 314 is attached to the frame portion 238 by any suitable fastening member, such as screws, pins, rivets or the like. The rotor loaded sensor 123 is attached to the sensor bracket 314 and positioned in relation to flag 298 such that flag portion 318 of flag 298 is positioned in opening 320 of sensor 316 when the engaging member 294 is in the disengaged position as is described in more detail below.

As further illustrated, the optical carriage assembly 124 includes an optical circuitry assembly 322 that is mounted in an optical transport frame 324. Specifically, the optical transport frame 324 includes guide rail openings 326 into which guide rails 134 (see also FIG. 2) are held. One of the guide rails 134 also passes through a corresponding guide rail opening 328 in the optical circuitry assembly 322, to thus slidably secure the optical circuitry assembly 322 to the optical transport frame 324 as is described in more detail below. Set screws 330 pass through corresponding set screw openings 331 in the optical transport frame 324 to secure the guide rails 134 in their respective guide rail openings 326 in the optical transport frame 324.

As further illustrated, a home flag 332 is attached to the optical transport frame 324 by screws 333 as shown. The significance of the leaf spring 332 is described below. A bolt 334 is assembled with a washer 336 and passes through bolt opening 338 in the optical transport frame 324. A threaded portion 340 of the bolt 334 is received into threaded opening 342 in the frame portion 238 to rotatably secure the optical transport frame and thus, rotatably secure the entire optical carriage assembly 124 to the frame portion 238. The frame portion 238 has machined surfaces 344 and 346 which allow the optical transport frame 324 to slide with respect to the frame portion 238 when the optical carriage assembly 124 is rotated about bolt 334. Screws 348 are assembled with respective washers 350, and the shaft portions of the screws are passed through slotted openings 352 in the optical transport frame 324 and are received into respective threaded openings 354 in the frame portion 238. An aligning screw 356 is threaded into a corresponding threaded opening 358 in frame portion 238, and an alignment spring plunger 360 is fit into a corresponding opening 362 in the frame portion 238.

During assembly of the optical carriage assembly 124 to the frame portion 238, the screws 348 are loosely screwed into the corresponding threaded openings 354 in the frame portion 238. The aligning screw 356 is then rotated further into opening 358 or further out of opening 358, as necessary, to rotate the optical carriage assembly 124 about bolt 334 to thus position the CCD array 128 in alignment with the LED bar 140 and for reading the centrifuged sample in the carrier tube in the rotor assembly 106 as is described in more detail below. That is, if the aligning screw 356 is screwed further into threaded opening 358, the end of the aligning screw 356 will abut against the optical transport frame 324 and rotate the optical transport frame 324 (and hence the optical carriage assembly 124) in a counterclockwise direction about bolts 334 when viewed from the top of the optical carriage assembly 124. Alternatively, if the aligning screw 356 is rotated further out of threaded opening 358, the force exerted on the optical transport frame 324 by the alignment spring plunger 360 will cause the optical transport frame 324 (and thus the entire optical carriage assembly 124) to rotate in a clockwise direction about bolt 334 when viewed from the top of the optical carriage assembly 124. Once the aligning screw 356 has been adjusted to place the CCD array 128 in the desired alignment, the screws 348 can be tightened into their respective openings 354 to secure the optical transport frame 324 and the entire optical carriage assembly 124 essentially immovably to the frame portion 238.

As further illustrated, the optical transport motor 132, which drives a gear 364, is coupled to the optical transport frame 324 by screws 366 and 368. Specifically, screw 366 passes through opening 370 in optical transport motor 132 and into corresponding opening 372 in the optical transport frame 324. Screw 368 is assembled to washer 374 and passes through slotted opening 376 in the optical transport motor 132, and is received into opening 378 in the optical transport frame 324. The slotted opening 376 enables the position of the optical transport motor 132 to be adjusted slightly before the screws 366 and 368 are fully tightened in their respective openings 372 and 378.

Figure 11:
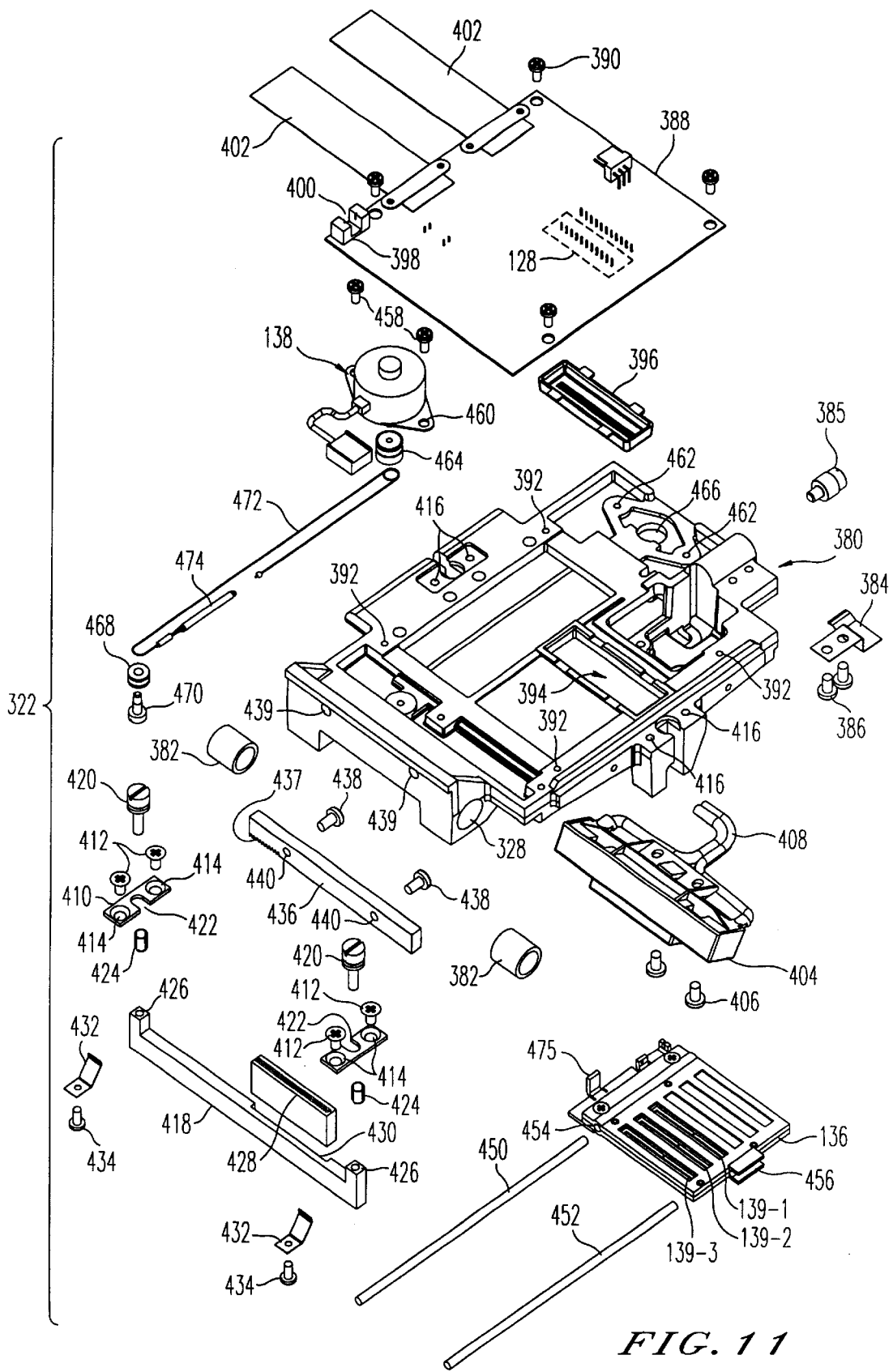
FIG. 11 is an exploded perspective view of the optical circuitry assembly of the optical carriage assembly shown in FIG. 10.
Figure 12:
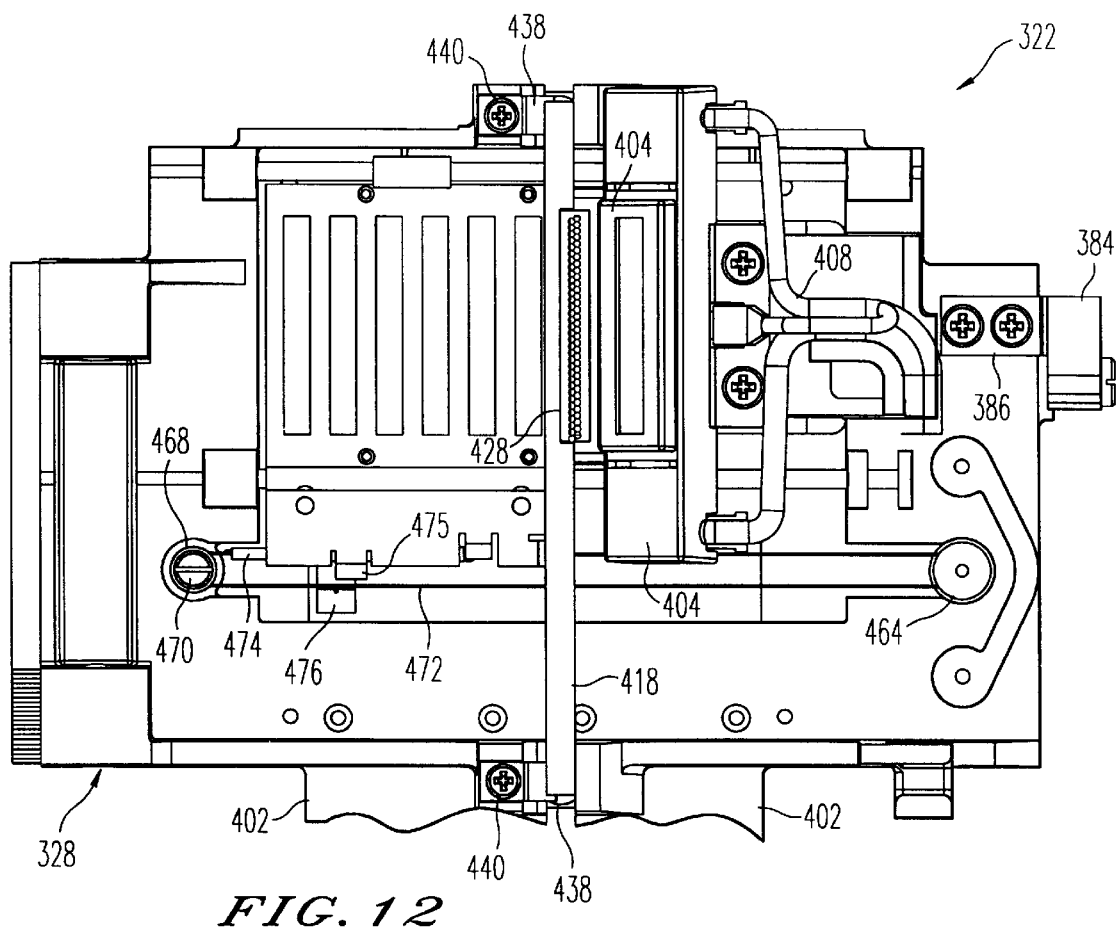
FIG. 12 is a bottom plan view of an assembled optical circuitry assembly shown in FIG. 11.
Figure 13:
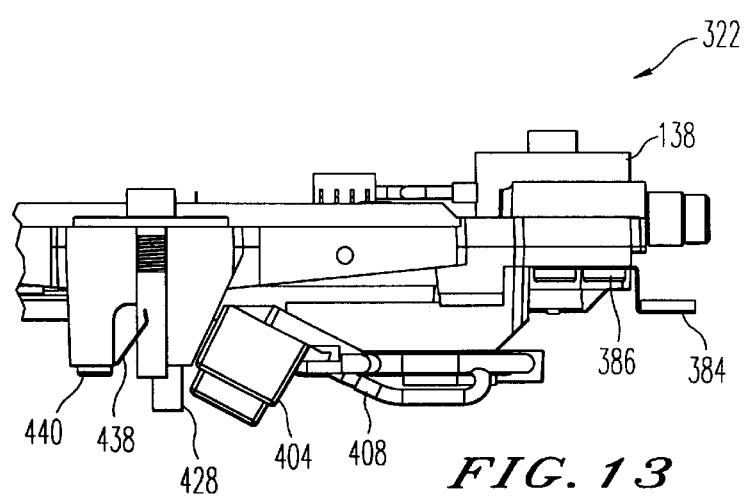
FIG. 13 is a front view of an assembled optical circuitry assembly shown in FIG. 11.

As shown in more detail in FIGS. 11–13, the optical circuitry assembly 322 includes an optics frame 380 which includes the guide rail opening 328 through which one of the guide rails 134 passes to slidably secure the optical circuitry assembly 322 to the optical transport frame 324. Bearings 382 are disposed inside the guide rail opening 328 at opposite ends of the guide rail opening 328. When the guide rail 134 passes through guide rail opening 328, the guide rail 134 also passes through the openings in bearings 382. The bearings 382 are made of nylon or any similar suitable material which reduces the friction between the portion of the surface of the optics frame 380 forming the guide rail openings 328 and the outer surface of guide rail 134, to thus allow the optics frame 380 to slide more freely along the guide rail 134.

A home flag 384 is mounted to optics frame 380 by fastening members 386, such as screws, rivets, pins or the like. A cam follower 385 is rotatably secured to the optics frame 380. The leaf spring 384 is positioned so that it contacts the bottom of corresponding guide rail 134, while cam follower contacts the top of that corresponding guide rail 134. Hence, the leaf spring 384 slides along the bottom of the corresponding guide rail 134, and the cam follower 385 rotates along the top of the guide rail 134, when the optical circuitry assembly 322 is being moved along the guide rails 134.

The optical circuitry assembly 322 further includes a CCD board assembly 388 that is secured to the optics frame 380 by screws 390, which are received into openings 392 in the optics frame 380. The CCD array 128 is mounted to the CCD board assembly 388 such that when the CCD board assembly 388 is mounted to the optics frame 380, the CCD array 128 is aligned with CCD opening 394 in the optics frame 380. A CCD shield 396 fits into opening 394 to cover and thus protect the CCD array 128.

The CCD board assembly 388 further includes an optical sensor 398 having a sensing opening 400. The optical sensor 398 and its sensor opening 400 is positioned so that when the optics circuitry assembly 322 is positioned in a "home" position along guide rails 134 as shown in FIG. 9, the leaf spring 332 attached to optical transport frame 324 enters sensor opening 400 and thus is detected by optical sensor 398. The CCD board assembly 388 further includes ribbon cables 402 through which signals are received from, for example, CPU 110 (see FIGS. 3 and 4), and through which signals are sent to, for example, CPU 110.

The optical circuit assembly 322 further includes a flash tube bracket 404 that is mounted to the optics frame 380 by screws 406. The flash tube 126 is mounted into flash tube bracket 404 as described in more detail in the aforementioned U.S. Pat. No. 6,030,086, Ser. No. 09/032,935. The cable 408 provides energizing power to the flash tube 126 as described in more detail below.

The optical circuitry assembly 322 further includes screw plates 410 that are mounted to the optics frame 380 by screws 412 which pass through corresponding openings 414 in the screw plates 410 and are received into corresponding openings 416 in the optics frame 380. A lens mount 418 is mounted to the optics frame 380 by screws 420 which pass through corresponding slots 422 in the screw plates 410, are assembled with corresponding compression springs 424, and are received into corresponding threaded openings 426 in the lens mount 418. A lens array 428 which is described in more detail below, is mounted in lens recess 430 in the lens mount 418 in a position where the lens array 428 is substantially aligned with the CCD array 128. Leaf springs 432 are mounted to the optics frame 380 by screws 434, so that the leaf springs 432 apply a force against lens mount 418 to help stabilize the lens mount 418 and thus help to restrain the lens array 428 from moving due to vibration.

The optical circuitry assembly 322 further includes a rack 436 having teeth 437 along its bottom the toothed plate 436 is secured to optics frame 380 by screws 438 which pass through corresponding openings 439 in the optics frame 380 and are received into corresponding openings 440 in the toothed plate 436. The teeth 437 engage with the gear 364 that is driven by optical transport motor 132 to move the optical circuitry assembly 322 in the direction indicated by arrow A in FIG. 9 and back again reverse to that direction.

The optical circuitry assembly 322 further includes a filter rack 136 which is described in more detail below and includes a green emission filter 138, a red emission filter 139 and a blue block filter 140. The filter rack 136 is slidably mounted to the optics frame 380 by guide bars 450 and 452. That is, guide bar 450 passes through opening 454 in the filter rack 136 and is mounted to the optics frame 380. Guide bar 452 passes through slot 456 in the filter rack 136 and is also mounted to the optics frame 380. Filter motor 138 is mounted to optics frame 380 by screws 458 which pass through corresponding openings 460 in the filter motor 138 and are received into corresponding openings 462 in the optics frame 380. The filter motor 138 drives a drive pulley 464 which is positioned in drive pulley opening 466 in the optics frame 380. Another drive pulley 468 is mounted to optics frame 380 by a screw 470. A filter drive cable 472 is coupled to a cable tension spring 474 and passes around drive pulleys 464 and 468. The cable tension spring 474 and the end of the filter drive cable 472 not connected to the cable tension spring 374 are connected to the filter rack 136. The filter motor 138 is electrically connected to the CCD board assembly 388 as shown, so that the filter motor 138 is driven in accordance with signals provided from the CCD board assembly 338 which, for example, have been provided by the CPU 110. As described in more detail below, the filter motor 138 rotates the drive pulley 464 to drive the filter drive cable 472 about pulley 468, and thus convey the filter rack 136 along guide bars 450 and 452 to position different ones of the filters 138, 139 and 140 in front of the lens array 428 for reasons discussed below. The filter frame bracket of the filter rack 136, to which the drive cable attaches, includes a home position flag 475 that is read by an interrupter 476 under the CCD board assembly 338 to detect the home position of the filter rack 136.

The operations for loading a carrier tube 114 into the centrifuge device 100 will now be described with regard to FIGS. 14–21, in particular.

Figure 14:
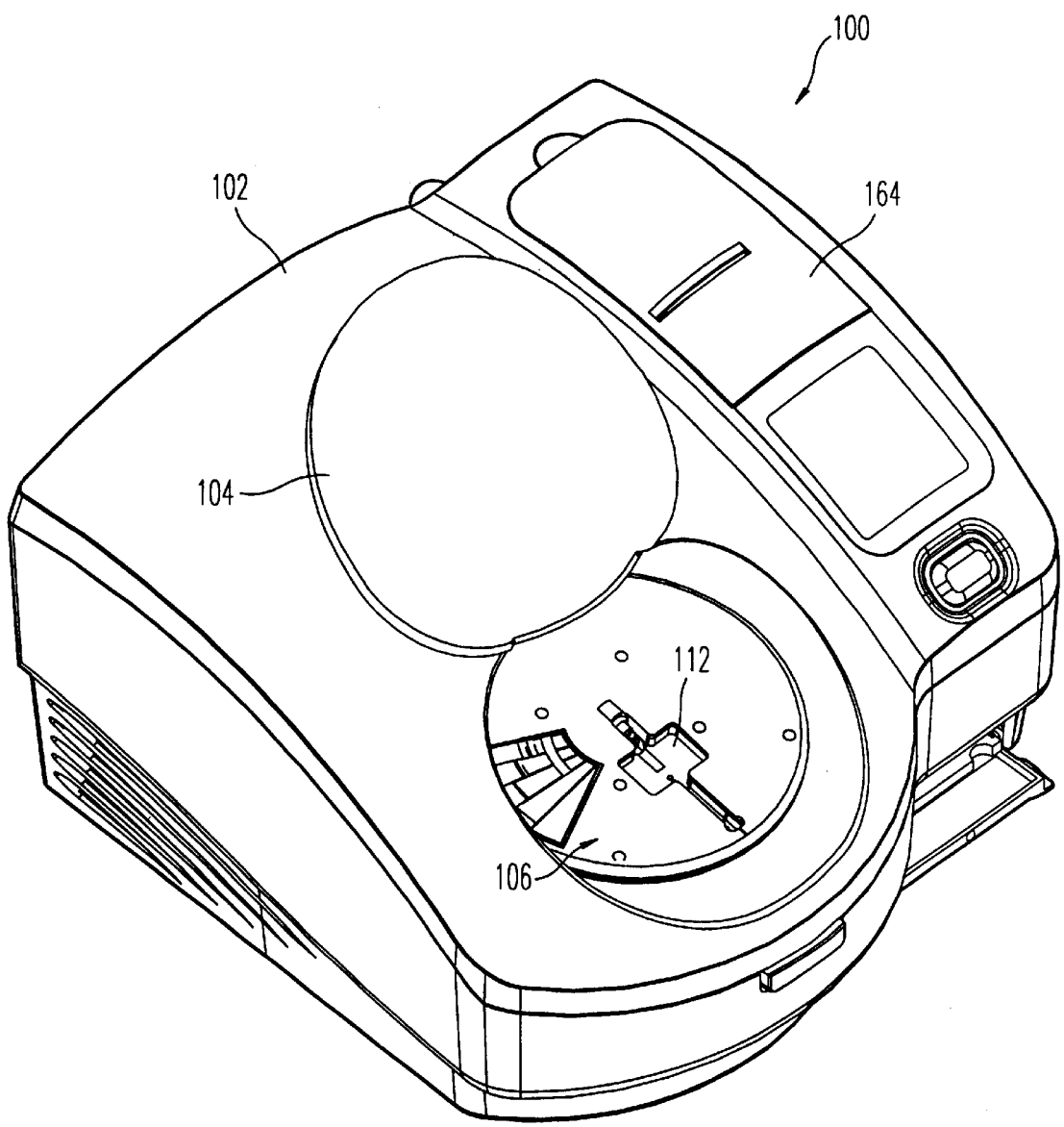
FIG. 14 is a perspective view of the centrifuge device shown in FIG. 1, but with the rotor assembly oriented in the tube loading and unloading position.

When a carrier tube 114 is ready for loading into the centrifuge device 100, an operator can enter a command via, for example, the key pad 162 so that the microcontroller 110 will control the motor 108 to rotate the rotor assembly 106 to the proper orientation for loading of the carrier tube 114, as can be determined through the use of the rotor assembly orientation sensor 135 as described below. This carrier tube loading orientation is essentially 180° from the orientation, which is shown in FIG. 14, of the rotor assembly 106 as shown in FIGS. 1 and 2.

To detect the orientation of the rotor assembly 106, the emitter in the emitter assembly 260 of the rotor assembly orientation sensor 135 emits a light signal toward the circumference of the rotor assembly 106. When the light pipe 200 is at a position such that the light being emitted by the rotor assembly orientation sensor 135 enters the light pipe 200 through light pipe side opening 202 and is redirected through the light pipe bottom opening 206, the light is detected by the detection in the detector assembly 262 of the rotor assembly orientation sensor 135. The rotor assembly orientation sensor 135 then provides a signal to the CPU 110, which interprets that signal as an indication that the rotor assembly 106 is oriented such that a carrier tube accommodating recess 112 is below the CCD array 128 and thus, a carrier tube 114 in the carrier tube accommodating recess 112 can be read by the CCD array 128. In using this detected orientation as a reference orientation, the CPU 110 can continuously monitor and ascertain the orientation of the rotor assembly 106 at all times when the rotor assembly is being rotated. Therefore, the CPU 110 can determine when the rotor assembly 106 in the tube loading and unloading position as shown in FIG. 12.

Figure 15A:
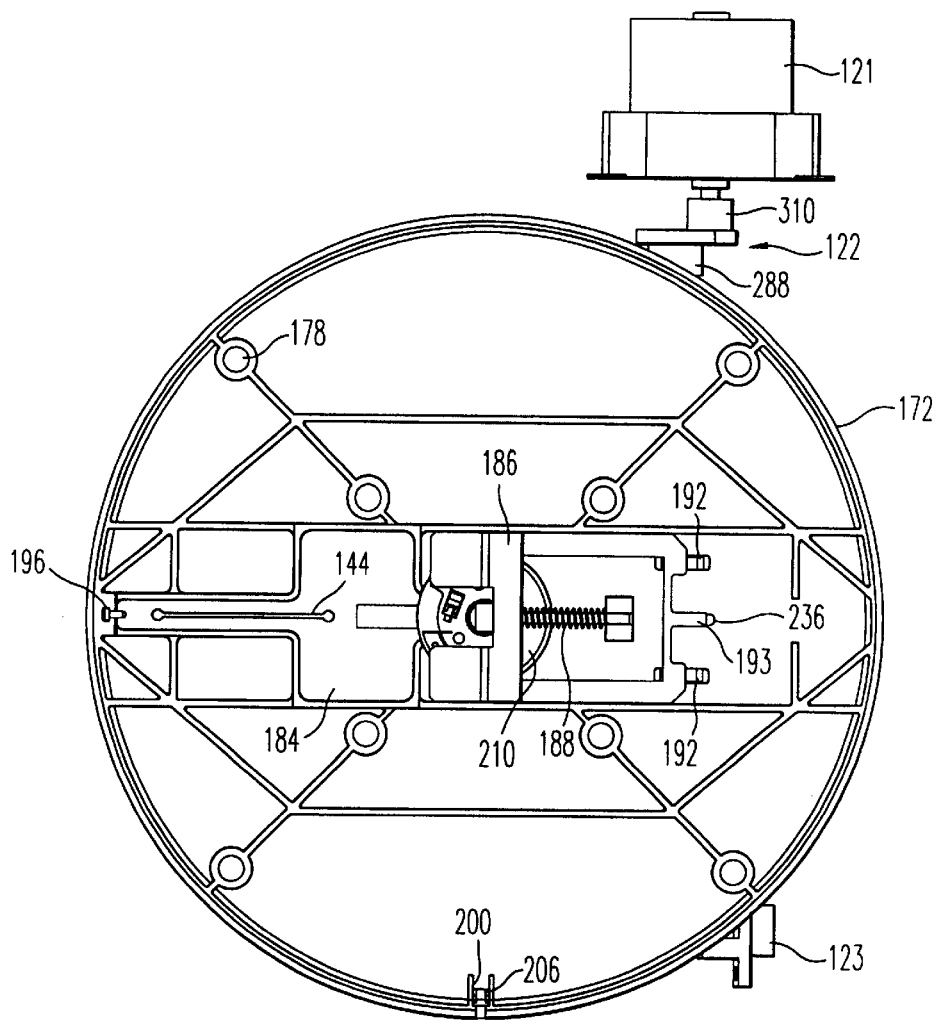
FIG. 15A is a top plan view of the rotor assembly shown in FIG. 5, with the top cover removed, in relation to the tube capture and release motor, and having the carrier tube holder assembly in the released position.
Figure 15B:
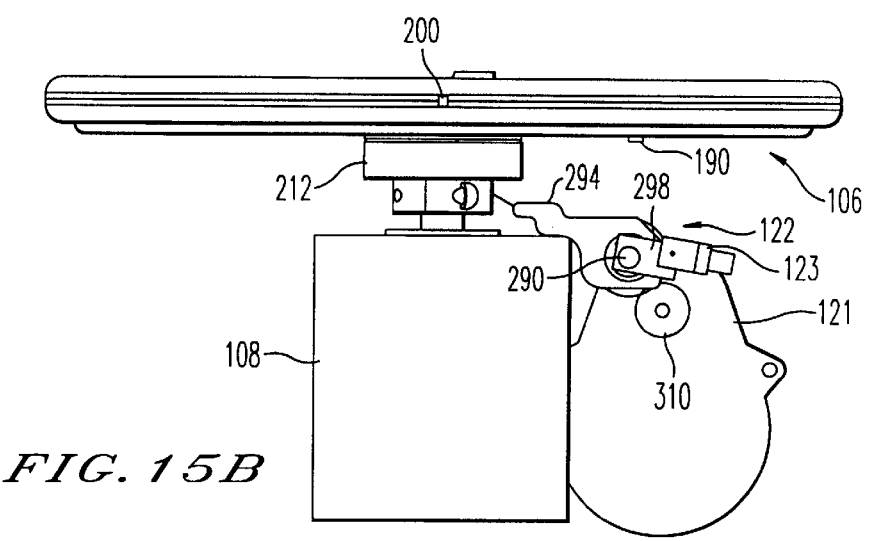
FIG. 15B is a side view of the rotor assembly shown in FIG. 5 with its cover attached, in relation to the tube capture and release motor and the engaging mechanism in the disengaged position.

FIG. 15A is a top plan view of the rotor assembly 106 as shown in FIG. 5, with the rotor top 170 being removed to expose the interior components of the rotor assembly 106, such as the carrier tube holder assembly 186, spring 188, pin 196, light pipe 200, and the index hub assembly 210. FIG. 15A also illustrates the tube capture and release motor 121 and gear 310, the engaging mechanism 122, and rotor loaded sensor 123. FIG. 15B is a side plan view further illustrating the relationship between the tube capture and release motor 121, the engaging mechanism 122 which includes gear 288, shaft 290, engaging member 294 and flag 298, rotor loaded sensor 123, the rotor assembly 106 with its top 170 attached, and the rotor motor 108.

Figure 16A:
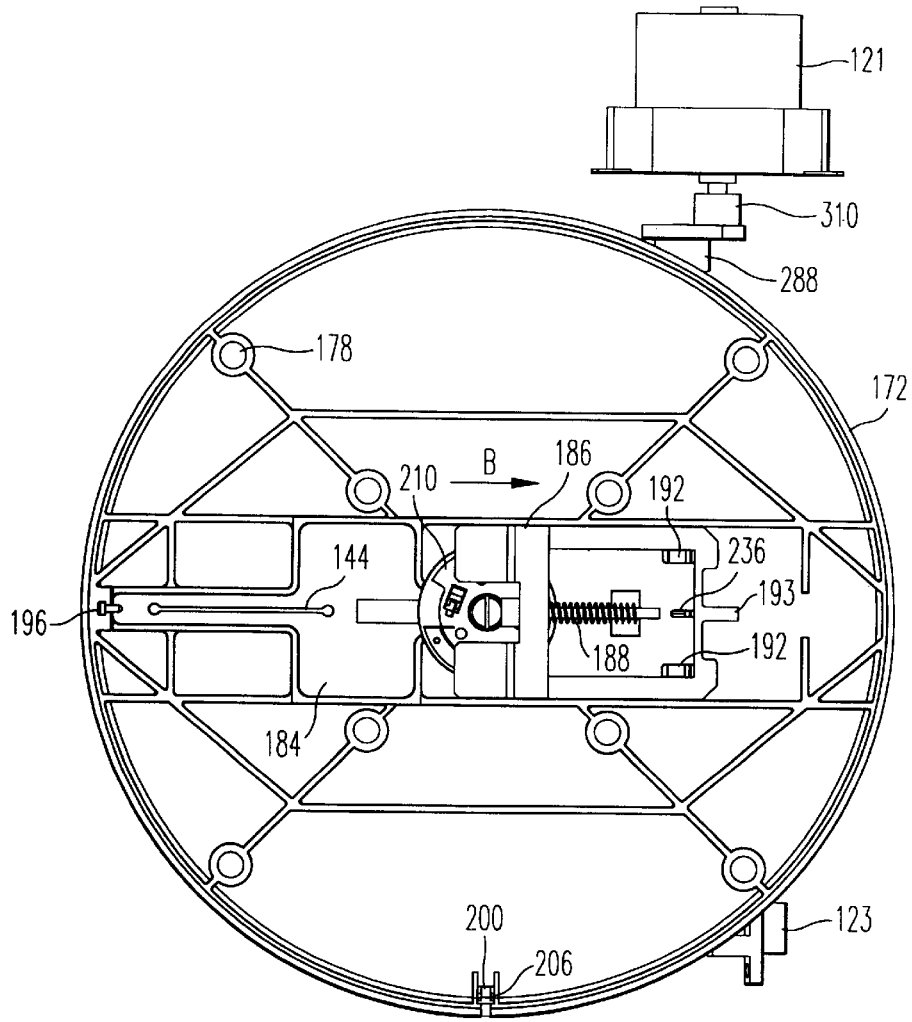
FIG. 16A is a top plan view of the rotor assembly and as shown in FIG. 10A, but with the tube holding assembly being positioned in the retracted position.
Figure 16B:
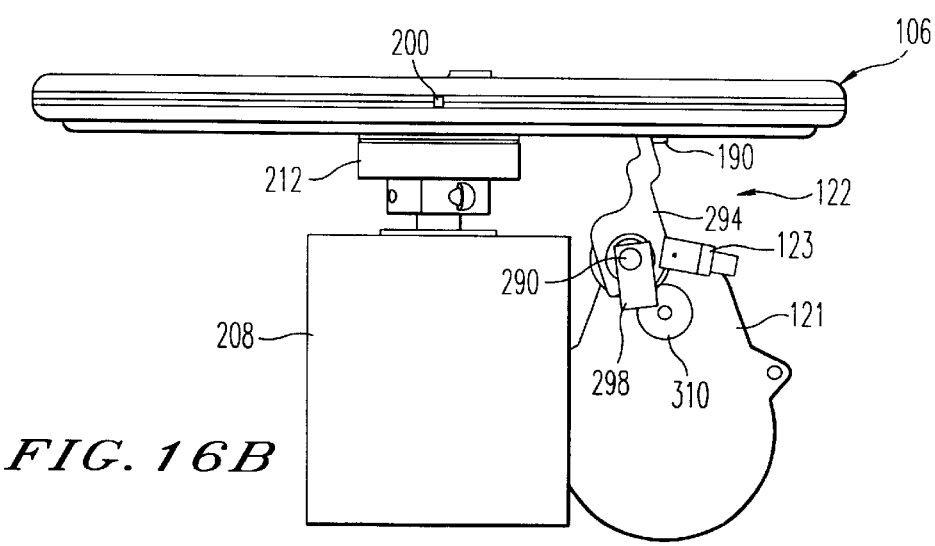
FIG. 16B is a side view of the rotor assembly, retractor assembly driving motor and the retractor assembly as shown in FIG. 10B, but with the retractor assembly driving motor engaging the retractor assembly.

When the rotor assembly 106 has been oriented to the tube loading orientation, the CPU 110 will control the tube capture and release motor 121 to drive the engaging mechanism 122 to engage legs 190 of the carrier tube holder assembly 186. Hence, as shown in FIGS. 16A and 16B, the engaging member 294 of the engaging mechanism 122 will pull the carrier tube holder assembly 186 in the direction indicated by arrow B in FIG. 16A against the force of spring 188. It is further noted that as long as the rotor assembly 106 is oriented so that the engaging member 294 engages at least one leg 190 of the carrier tube holder assembly 186, the force exerted on that one leg 190 by the engaging member 294 will be sufficient to rotate rotor assembly 106 as necessary to orient the rotor assembly 106 so that the engaging member 294 will also engage the other leg 190. When the carrier tube holder assembly 186 is in the position indicated in FIG. 16A, a carrier tube 114 can be loaded into the carrier tube accommodating recess 112 of the rotor assembly 106.

Figure 17:
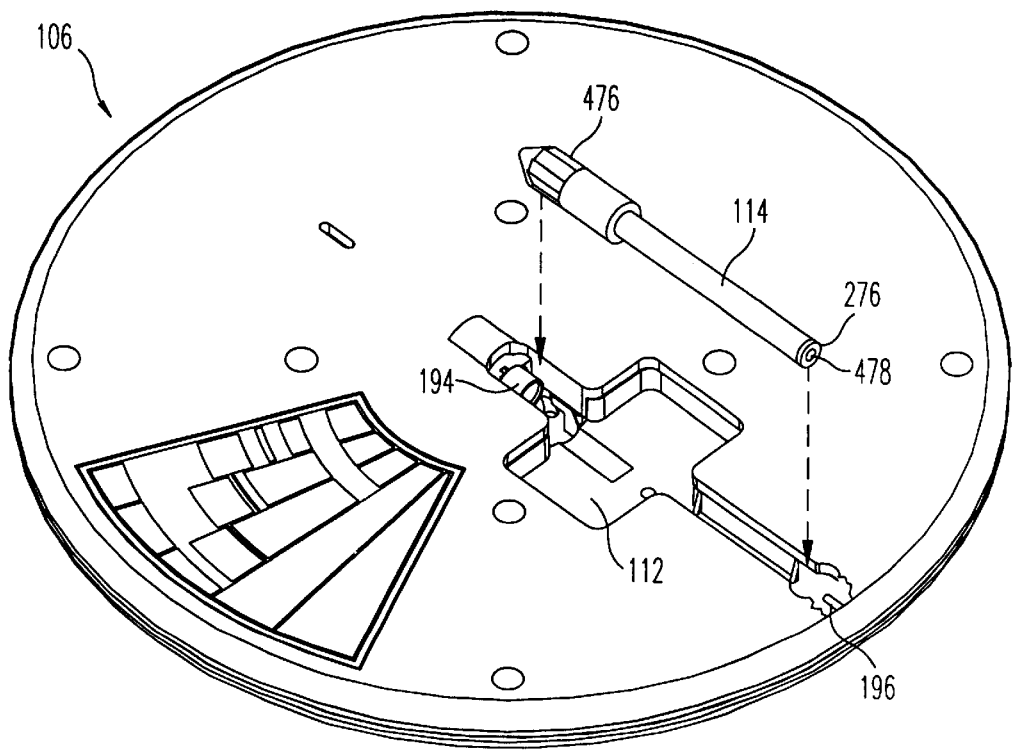
FIG. 17 is a detailed assembled perspective view of the rotor as shown in FIG. 5, with a carrier tube about to be inserted into the carrier tube accommodating recess.
Figure 18:
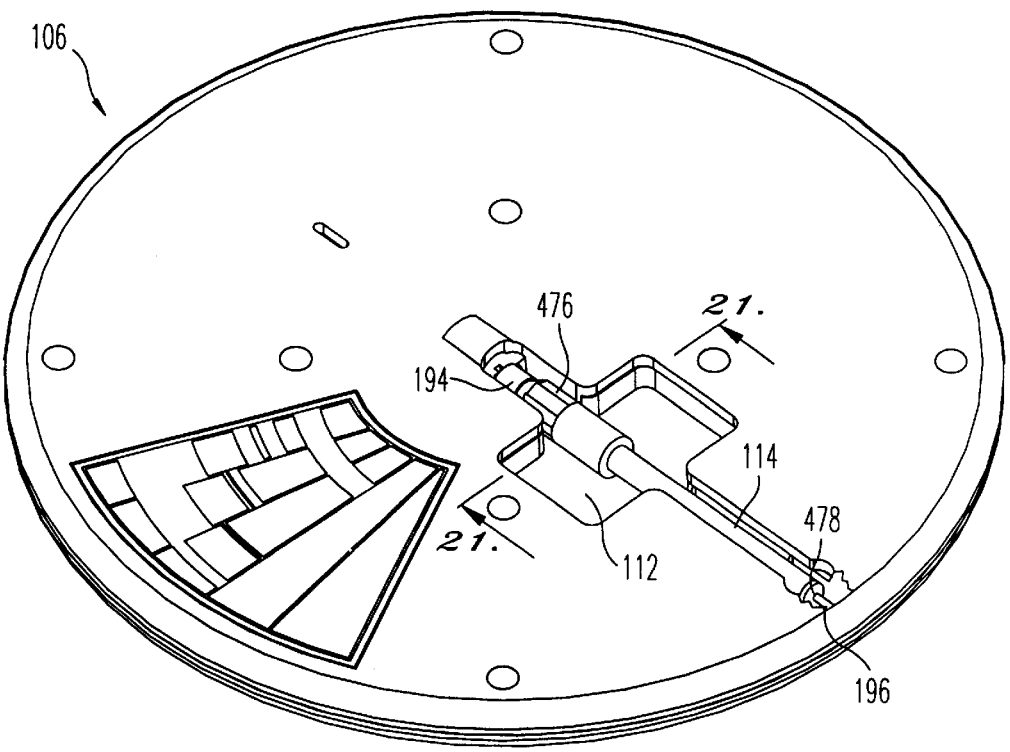
FIG. 18 is a detailed assembled perspective view of the rotor as shown in FIG. 5, with the carrier tube inserted in the carrier tube accommodating recess.

That is, the CPU 110 can operate the door release and lock mechanism 116 (see FIG. 2) to release the door 104 of the centrifuge device 100 so that the door 104 can be opened to provide access to the rotor assembly 106. As shown in FIGS. 17 and 18, the carrier tube 114 can then be loaded into the carrier tube accommodating recess 112 in the rotor assembly 106 such that the front portion of the geared cap 476 of the carrier tube 114 having gear teeth 275 is received into cup 194.

Once the carrier tube 114 has been loaded into the carrier tube accommodating recess 112, the door 104 of the centrifuge device 110 can then be shut, and the centrifuge device 100 is ready to perform the centrifugation on the sample in the capillary tube contained in the carrier tube 114. The operator presses the start button 156 to instruct the CPU 110 to control the tube capture and release motor 121 to drive the engaging member 294 of the engaging mechanism 122 back to the position shown in FIG. 15B. When this occurs, the force applied by the spring 188 to the carrier tube holder assembly 186 moves the carrier tube holder assembly 186 in the direction opposite to arrow B in FIG. 16A. The pin 196 in the rotor assembly 106 then engages an opening 478 at the bottom end of the carrier tube 114. Hence, the pin 196 and the cup 194 secure the carrier tube 114 in the carrier tube accommodating recess 112 at both ends of the carrier tube 114.

Figure 19:
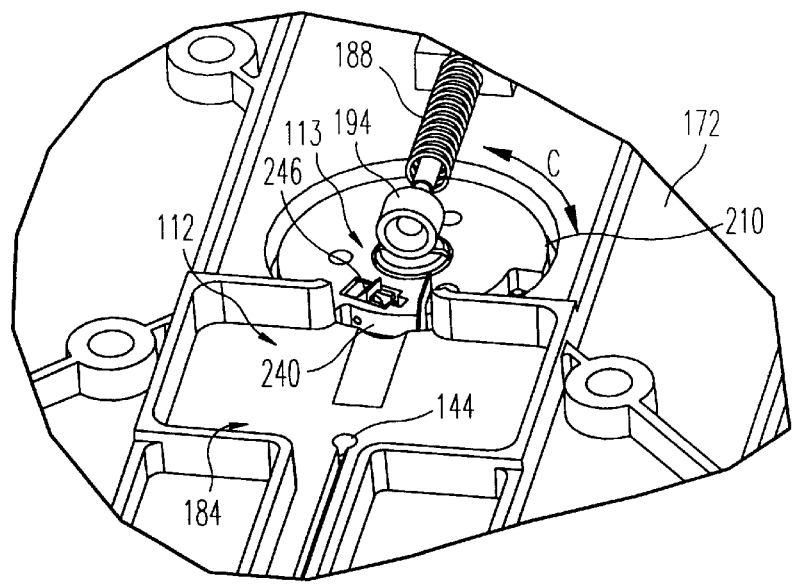
FIG. 19 is a detailed perspective view of the carrier tube accommodating recess, indexing mechanism and tube holding assembly of the rotor assembly as shown in FIG. 5.
Figure 20:
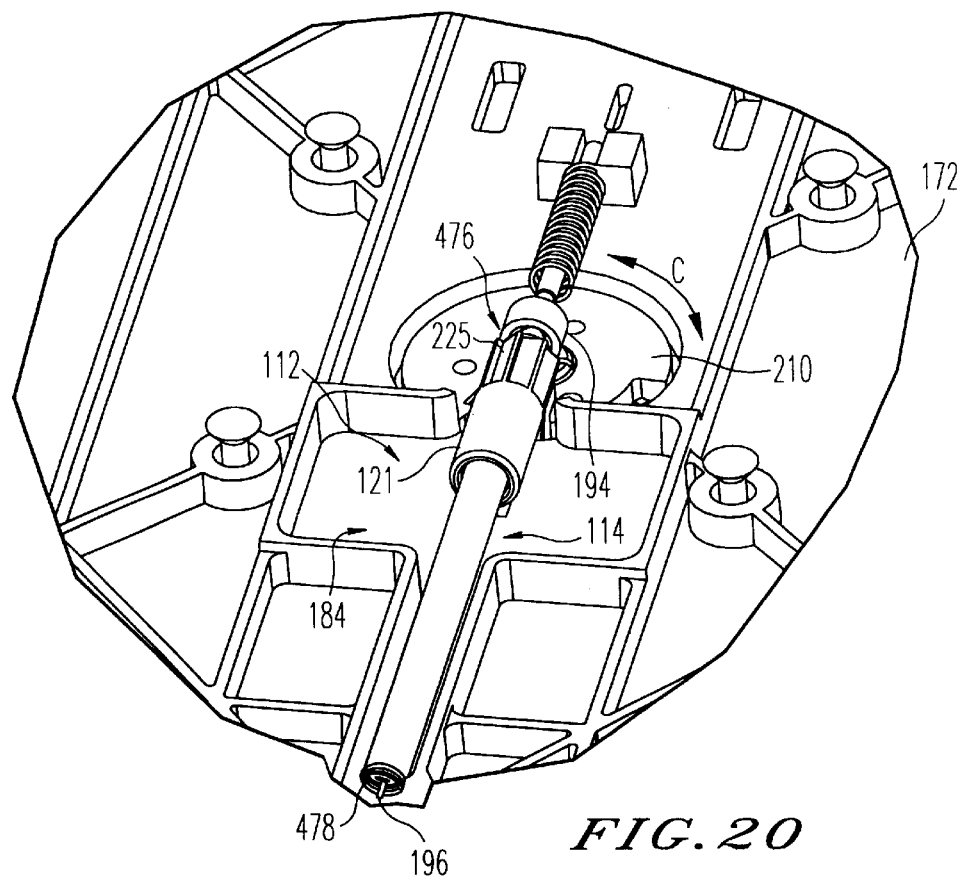
FIG. 20 is a detailed perspective view of the carrier tube accommodating recess and tube holding member of the rotor assembly as shown in FIG. 5, with a carrier tube being inserted in the carrier tube accommodating recess.
Figure 21:
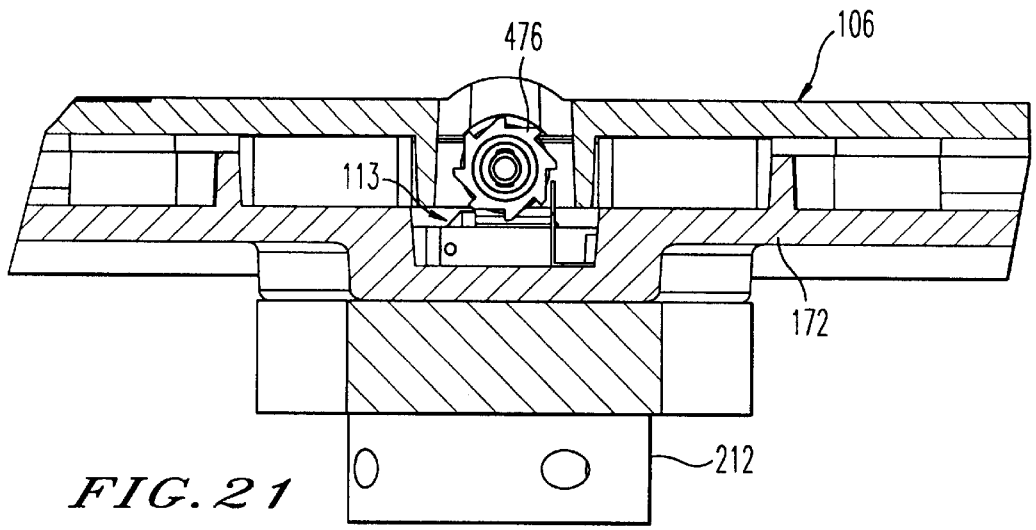
FIG. 21 is a detailed cross-sectional view of the rotor assembly having a carrier tube inserted in the carrier tube accommodating recess as taken along lines 21—21 in FIG. 18.

Placement of the carrier tube 114 in the carrier tube accommodating recess 112, and the relationship of indexing mechanism 113 and the geared cap 476 of the carrier tube 114 can be further appreciated from FIGS. 19 and 20. As shown in FIG. 19, the index hub assembly 210 is oriented such that the indexing mechanism 113 is positioned as indicated. As discussed above, index hub assembly 210 can rotate with respect to the rotor bottom 172 in the direction indicated by arrow C as limited by the limit pins 216. The cut-out portion 213 of the index hub assembly 210 is positioned as indicated to provide clearance for the pawl 208 when the index hub 210 rotates. As shown in FIG. 20, when the carrier tube 114 is loaded into the carrier tube accommodating recess 112 and rests in the cavity 184 in the rotor bottom 172, the front end of the geared cap 476 of the carrier tube 114 is received in cup 194 and the pin 196 is received into the opening 478 at the opposite end of the carrier tube 114. FIG. 21, which is a cut away view of the rotor assembly 106 having the carrier tube 114 mounted therein as shown in FIGS. 18 and 20, illustrates the relationship between the indexing member 113, the pawl 208 and the geared cap 476 of the carrier tube 114 more explicitly.

The operations pertaining to the centrifugation of the sample in the capillary tube contained in carrier tube 114, as well as the reading of the centrifuged sample as performed by the centrifuge device 100, will now be described with reference to FIGS. 22–32 in particular.

Figure 22:
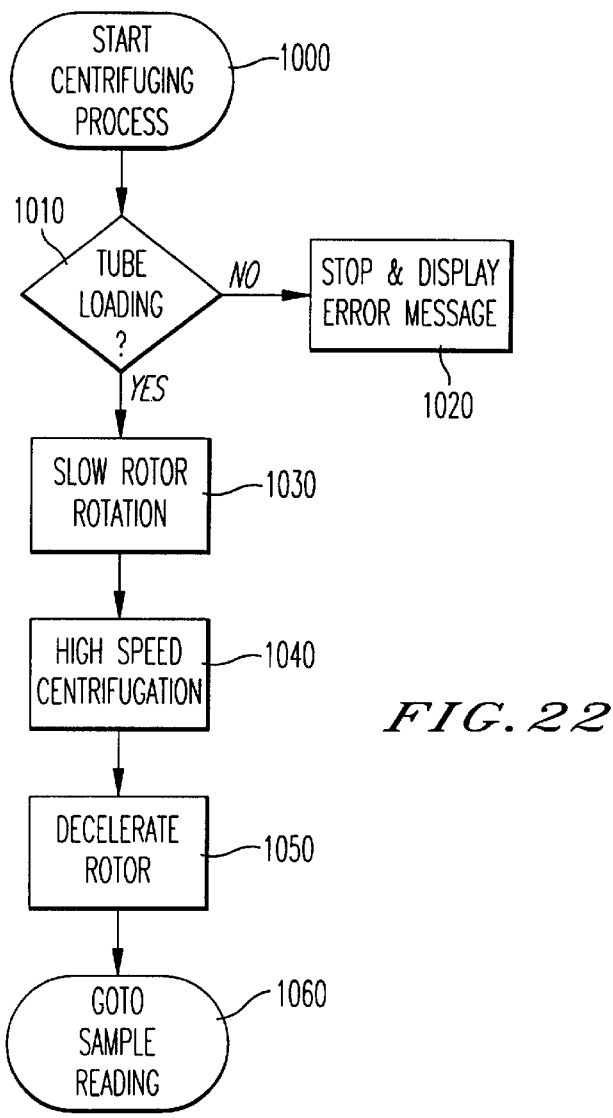
FIG. 22 is a flowchart illustrating an example of steps performed by the centrifuge device shown in FIG. 1 when performing centrifugation.
Figure 23:
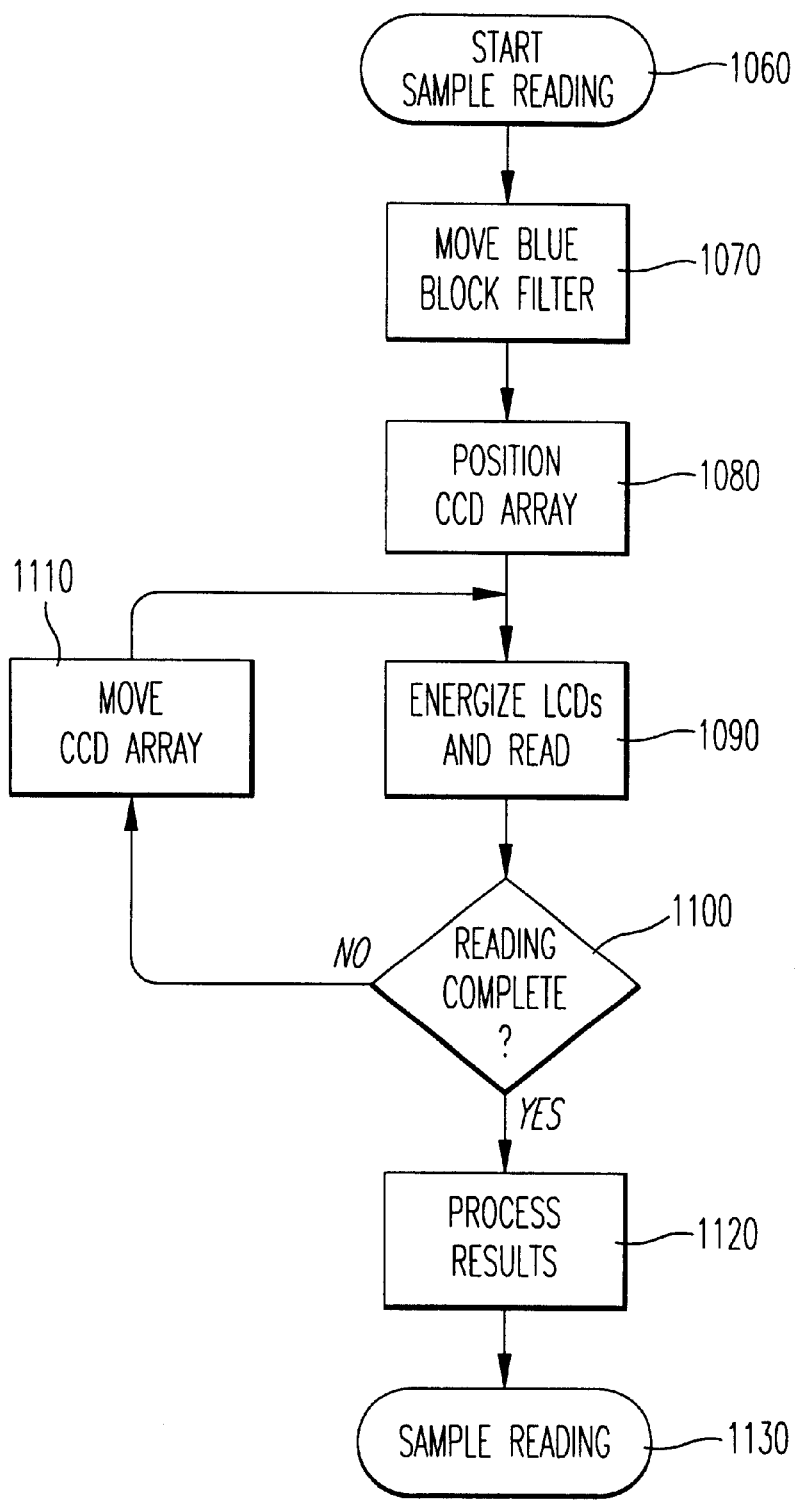
FIG. 23 is a flowchart illustrating an example of the steps performed by the centrifuge device when performing the LED transmission readings.

After the carrier tube 114 which holds the capillary tube containing the sample (e.g., uncoagulated blood) is loaded into the rotor assembly 106 in the manner described above, starting in step 1000 in the flowchart shown in FIG. 22, the centrifuge device 100 can begin the centrifuging process to centrifuge the sample to separate the components of the sample into individual layers. It is noted that when the centrifuge device 100 has initially been activated, it can spin the rotor 106 to perform a calibration of the optics using the calibration decal 115. Initially, after the door 104 has been closed, the CPU 110 can control the drive board 111 to drive the LED bar 141 (see FIGS. 3 and 4) to emit light toward to bottom of the rotor assembly 106 in step 1010. If the CCD array 128 detects light through the slit 142 in the top of the rotor assembly 106 when the corresponding slit 236 in the rotor bottom 172 is above the LED bar 141 when the rotor assembly 106 is at the tube loading and unloading orientation as shown in FIG. 14, the CPU 110 could interpret this detection as an indication that the carrier tube holder assembly 186 has not properly engaged the carrier tube 114.

That is, as can be appreciated from FIGS. 15A and 16A, when the carrier tube 114 has been loaded properly in the carrier tube accommodating recess 112 and is engaged properly with the tube holder assembly 186, the projection 193 will obstruct the opening 236, so that essentially no light emitted by the LED bar 140 will be allowed to pass through slit 142 in the rotor top 170 when corresponding slit 236 in the rotor bottom 172 is over LED bar 141. However, if the carrier tube 114 is not held properly by the carrier tube holder assembly 186, or the geared cap 476 is not properly capped onto the carrier tube projection 193 of the tube holder assembly 186 will not completely obstruct slit 236. In this event, light will pass through slit 236 at the edge of the slit 236 closest to the carrier tube 114 if the cap 476 is not on the tube far enough, and at the edge of the slit 236 furthest from the carrier tube 114 if the cap 476 is too far on the tube (e.g., if the glass capillary tube is fractured). The light will then pass through corresponding slit 142, and thus be detected by CCD array 128. The CPU 110 will interpret this detection as indicating improper carrier tube loading, and thus, will take corrective action, such as proceeding to step 1020 to display an error message on the LCD display 146 and prevent rotation of the rotor assembly 106.

Presuming that the CCD array 128 has not detected any light from the LED bar 140 passing through slit 142, the CPU 110 can interpret this non-detection of light as an indication that the carrier tube 112 has been loaded properly in the rotor assembly 106. The CPU 110 can then control the rotor motor 108 in step 1030 to begin rotating the rotor assembly 106, and can control the CCD array 128 (see FIGS. 2–4) to detect for the presence of the light emitted by the LED bar 141 at the appropriate respective times when the slits 144 and 236 are directly over the LED bar 141. That is, during the initial rotation period which lasts for about 1 minute, the CPU 110 controls the rotor motor to rotate the rotor assembly 106 at a relatively slow speed (e.g., 1000 r.p.m.). This slow rotation gently forces the blood in the capillary tube contained in the carrier tube 114 into contact with the dried reagents in the sample tube, which is described in more detail in the aforementioned copending U.S. Pat. No. 6,080,366 to King et al. entitled "Disposable Blood Tube Holder". This slow rotation also causes the float in the sample tube to descend from the top of the tube toward the plugged end of the tube. The CPU 110 can control the LED bar 140 to emit light towards the bottom of the rotor assembly 106 at, for instance, the corresponding times that the slits 144 and 236 are directly over the LED bar 140. If the CCD array 128 detects light from the LED bar 141 when the opening 144 is over the LED bar 141, the CPU 110 will interpret this light detection as an indication that a carrier tube 114 is not present in the carrier tube accommodating recess 112. If, for example, the CPU 110 detects that the carrier tube 114 is no longer present in the carrier tube accommodating recess 112 while the rotor assembly 106 is being rotated, the CPU 110 can interpret this as an indication that the carrier tube 114 has become dislodged from the cup 194 and pin 196, and has possibly been ejected from the rotor assembly 106. In this event, the CPU 110 can, for example, control the LCD display 146 to display an error message, and control the rotor motor 108 to discontinue rotation of the rotor assembly 106.

On the other hand, if the CCD array 128 detects light through slit 142 in the top of the rotor assembly when the corresponding slit 236 in the bottom of the rotor assembly 106 is above the LED bar 140, the CPU 110 could interpret this detection as an indication that the carrier tube 114 is no longer properly being held by the carrier tube holder assembly 186. The CPU 110 could then take corrective action, such as displaying an error message on the LED display 146 and stopping rotation of the rotor assembly 106.

Presuming that none of these problems have occurred, and therefore, the carrier tube 114 remains properly loaded in the carrier tube accommodating recess 112, the CPU 110 will begin to perform the high speed centrifugation process in step 1040. That is, the CPU 110 will control the rotor motor 108 to accelerate rotation of the rotor assembly 106 until the rotor motor 108 rotates the rotor assembly at a speed of approximately 11,000 r.p.m. This acceleration to 11,000 r.p.m. takes approximately 10 seconds to occur. The rotor motor 108 will rotate the rotor assembly 106 at this nominal speed of approximately 11,000 r.p.m. for approximately 3 minutes (e.g., 170 seconds). This high speed rotation creates a force of approximately 14,000 g at the rim of the rotation assembly 106 to separate and pack the cells in the blood sample in the sample tube contained in the carrier tube 114 into 5 distinct packed cell bands. The rotational speed of the rotor assembly 106, as well as the high speed centrifugation time, naturally can be changed as desired. Also, during the high speed centrifugation, the CPU 110 can continue to control the LED bar 140 and CCD array 128 in the manner described above to detect whether the carrier tube 114 has become improperly held in the rotor assembly 106 or dislodged from the rotor assembly 106.

The CPU 110 then proceeds to step 1050 where the rotation of the rotor assembly 106 down to approximately 2,400 r.p.m. This deceleration to approximately 2,400 r.p.m. takes about 10 seconds. The CPU 110 will then proceed to step 1060 to begin performing the steps for reading the centrifuged blood sample in the sample tube contained in the carrier tube 114 as described with regard to the flowchart in FIG. 23.

Figure 24:
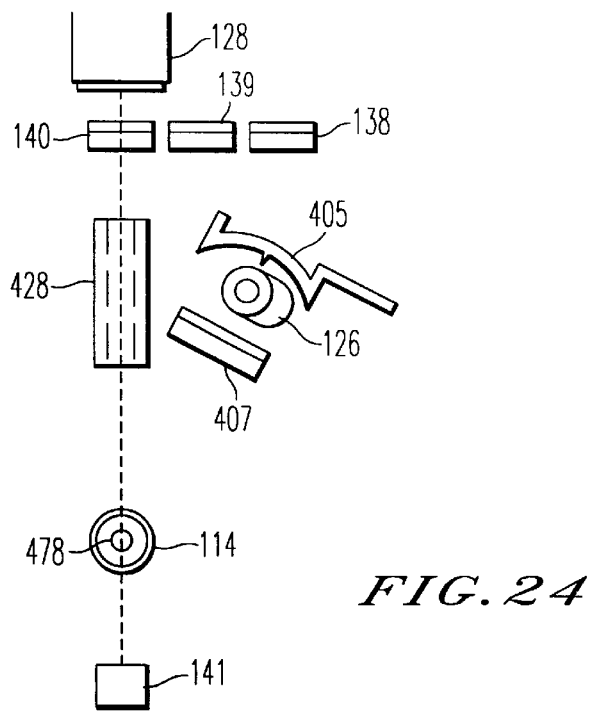
FIG. 24 is a schematic illustrating the relationship between the flash tube, arc guide, CCD array, filters, LED bar and carrier tube when the rotor assembly positions the carrier tube and the CPU energizes the LED bar for reading the centrifuged blood sample by the LED transmission as described with regard to FIG. 23.

The relationship between the CCD array 128, flash tube 126, arc guide 405, blue excitation filter 407, lens array 428, filters 138, 139 and 140, LED bar 141, and the carrier tube 114 is shown in a schematic in FIG. 24. This figure also illustrates the sample tube 478 which contains the blood sample and which is in the carrier tube 114.

Figure 25:
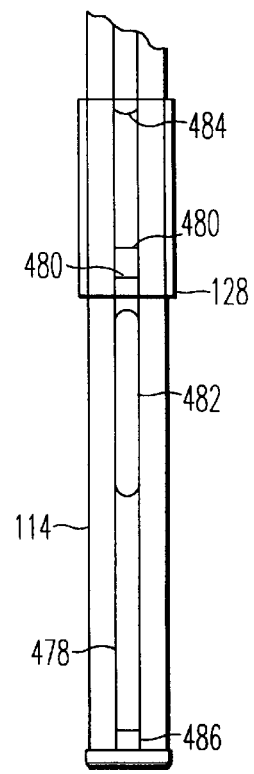
FIG. 25 is a top view of the schematic shown in FIG. 22 illustrating the relationship of the CCD array and carrier tube when a first portion of the centrifuged sample in the carrier tube is being read.

In step 1070, the CPU 110 controls the filter motor 137 to drive the filter rack 136 along guide bars 450 and 452 as discussed above with regard to, for example, FIG. 11, until the blue block filter 140 is positioned in front of the CCD array 128 as shown in FIG. 24. At this time, the CPU 110 in step 1080 also controls the optical transport motor 132 to move the optical circuitry assembly 322 to the far end of the guide rails 134 so that the CCD array 128 is positioned as shown in FIG. 25 to read the portion of the sample at the end of the sample tube 478 closest to the cap 476 (not shown).

This figure also illustrates the fill lines 480 present on the sample tube, and the float 482 in the sample tube 478. It is noted that the optical sensor 398 (FIG. 11) on the optical circuitry assembly 322 detects the leaf spring 332 on the optical transport frame 324 when the optical circuitry assembly 322 is in this position, and provides an appropriate signal to the CPU 110 so the CPU 110 can stop movement of the optical circuitry assembly 322.

When the CPU 110 determines from the signals provided by the rotor assembly orientation sensor 135 that the rotor assembly is oriented such that the carrier tube 114 is in a position to be read (i.e., in a position essentially directly below the CCD array 128), the CPU 110 will energize the LED bar 141 in step 1190 to emit light toward the rotor bottom 172. That light passes through slit 144 in the rotor bottom (see, for example, FIGS. 2 and 3) and impinges on carrier tube 114. A portion of the light emitted by LED bar 141 will be absorbed by the centrifuged sample, float, and plug in the blood tube contained in the carrier tube 114. The light that is not absorbed passes through carrier tube 114, through lens array 428 and enters the blue block filter 140. The blue block filter prevents essentially all light having a wavelength less than 530 nm from passing through the filter 140 and being received by the CCD array 128. Primarily, the blue block filter 140 functions to prevent blue light of the stroke excitation source (i.e., flash tube 126 and blue excitation filter 407) from entering the CCD array 128.

Figure 26:
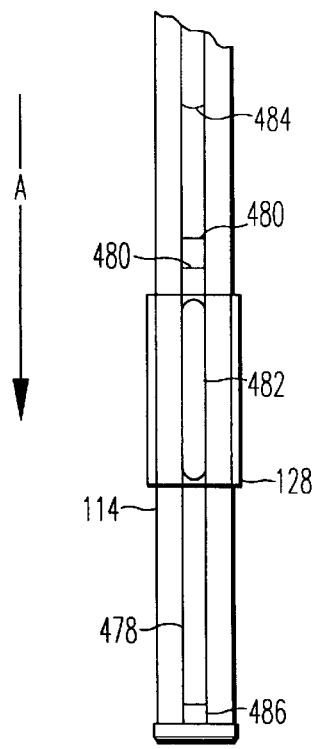
FIG. 26 is a top view as in FIG. 25 with the CCD array being moved to a position to read a second portion of the centrifuged sample in the carrier tube.

As shown in FIG. 24, when the above reading has been taken, it is noted that the length of the CCD array 128 will enable it to receive the light from only about ⅓ of the length of the centrifuged sample in the sample tube contained in the carrier tube 114. Therefore, in step 1100, the CPU 110 will determine if all of the desired reading has been completed. If not, the CPU 110 will control the optical transport motor 132 to step 1110 to move the optical circuitry assembly 322 (and thus the CCD array 128) along guide rails 134 in the direction indicated by arrow A in FIGS. 3, 9 and 24, until the CCD array 128 is positioned as shown in FIG. 26.

Figure 27:
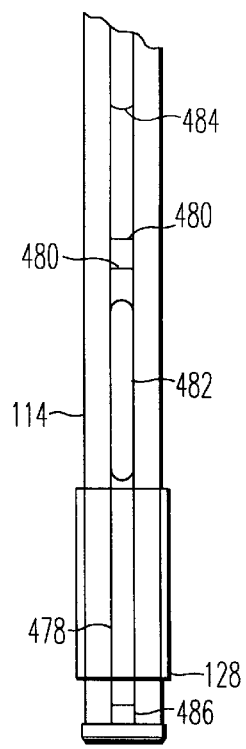
FIG. 27 is a top view as shown in FIG. 25 with the CCD array being further moved to another position to read a third portion of the centrifuged sample in the carrier tube.

The CPU 110 then returns to step 1090 as described above. The CPU 110 will determine when the carrier tube 114 is in a position for reading, and in step 1090 energize the LED bar 141, and control the CCD array 128 to detect the unabsorbed portion of the light. The CPU 110 will then determine in step 1100 whether the reading is complete. If not, the CPU 110 will proceed to step 1110 where it will control the optical transport motor 132 to move the CCD array 128 further in the direction indicated by arrow A in FIGS. 3, 9 and 26 so that the CCD array 128 is positioned as shown in FIG. 27. The CPU will then return to step 1190, where it will control the LED bar 141 to emit light as described above, and control the CCD array 128 to detect the light passing through the sample in the carrier tube 114.

The CPU 110 will then determine in step 1100 that the initial reading process has been completed, and proceed to calculate results based on these initial reads in step 1120. Specifically, these initial LED transmission readings are performed to locate the two fill lines 480 on the blood tube 478 which contains the centrifuged blood sample to verify the size of the blood tube 478. That is, with conventional blood tubes, the location of the fill lines is an indicator to the type of the blood tube. The fill lines 480 will block the light emitted from the LED bar 141 from passing through the blood tube 478, and thus, the CCD array 128 will be able to detect the absence of the light in proportion to the width and position of the fill lines. If the CPU 110 determines based on the detected readings of the fill lines that an improper type of blood tube is being used, the CPU 110 can cause the graphics display 146 to display an error message, for example. Also, by determining the type of the blood tube based on the width of the fill lines, the CPU 110 will determine the appropriate formula needed to calculate the cell counts in the layers for that size tube.

The LED transmission readings also detect the position of the float 482 as it is suspended in the blood tube. The details of the float and blood tube can be found in the aforementioned related U.S. Pat. No. 6,080,366 to Kelly et al. entitled "Disposable Blood Tube Holder". Since the float 482 occupies some volume in the blood tube, the level of centrifuged blood in the blood tube will have risen above the fill lines 480. Nevertheless, because the volume of the float 482 is known, the CPU 110 will be able to determine based on the position of the meniscus 484 in relation to the fill lines (as is detected as described below) whether the blood tube has been filled with the proper amount of blood. This entire process for performing these initial transmission readings can take approximately 5 seconds.

Figure 28:
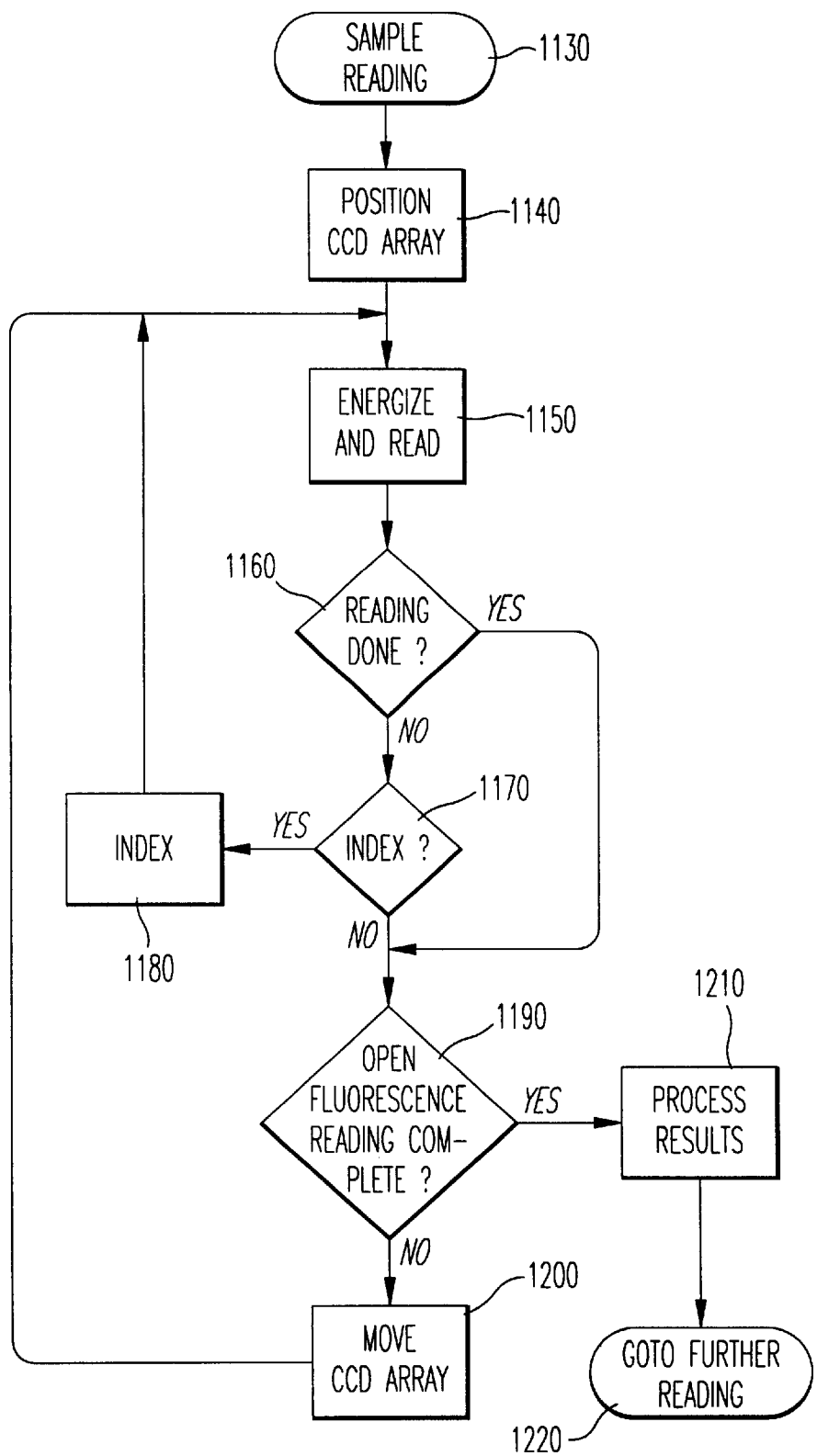
FIG. 28 is a flowchart showing an example of the steps performed by the centrifuge device when performing open fluorescence readings.
Figure 31:
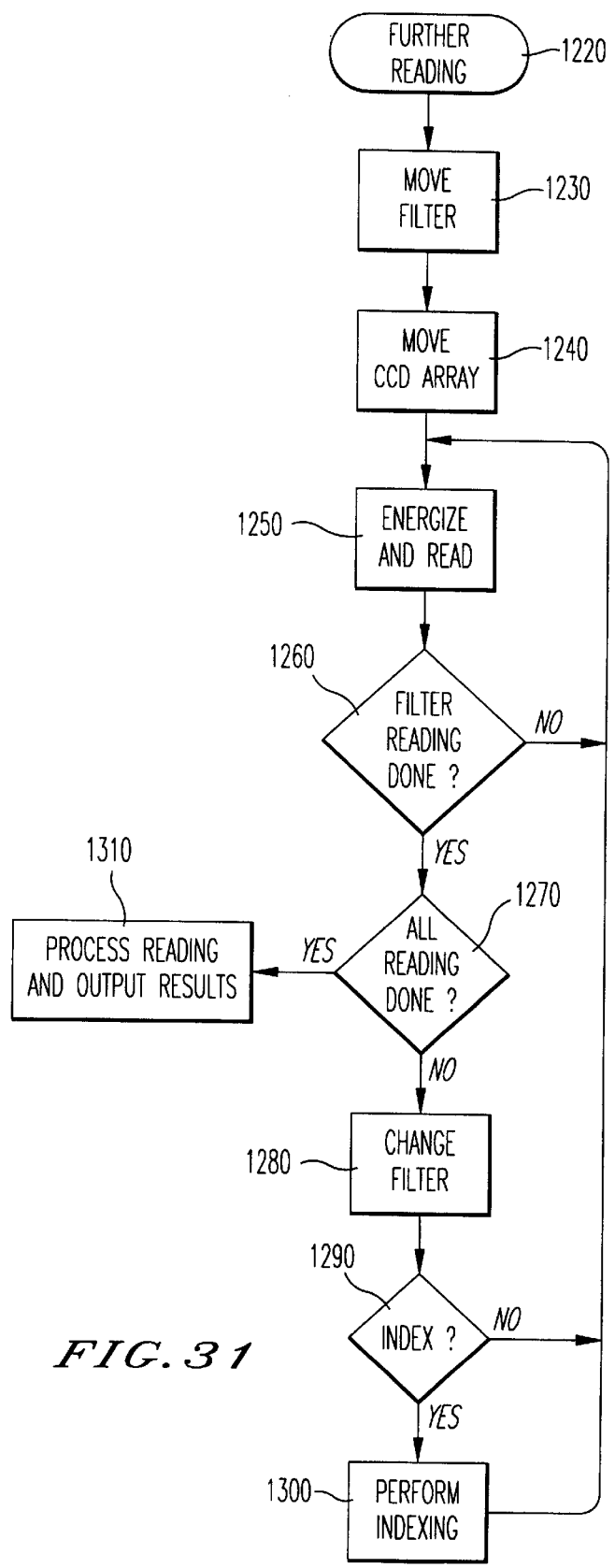
FIG. 31 is a flowchart showing an example of the steps performed by the centrifuge device when performing green emission readings, red emission readings and indexing.

The CPU 110 will then proceed to the sample reading process beginning at step 1130 as shown in the flow chart of FIG. 28. The CPU 110 will initially perform an open fluorescence reading process beginning at step 1130. In doing so, the CPU will select the appropriate filter to be positioned in front of the CCD array 128. As shown in FIGS. 29A–29C, the CPU 110 can control the filter motor 137 to position the blue block filter 140 in front of the CCD array 128 (FIG. 29A), to position the green emission filter 138 in front of the CCD array 128 (FIG. 29B), and to position the red emission filter 139 in front of the CCD array 128 (FIG. 29C). In this example, the CPU 110 causes the filter motor 137 to keep the blue block filter 140 in front of the CCD array 128, as shown in FIG. 29A. In step 1140, CCD array 128 is returned to the position in relation to the carrier tube 114 as shown in FIG. 25.

When the CPU 110 determines based on the signals provided by rotor assembly orientation sensor 135 that the rotor assembly 106 is oriented so that the carrier tube 114 is in position so that the centrifuge sample in the blood tube can be read, the CPU 110 in step 1150 controls the flash tube 126 to emit light. As shown in FIG. 29A, the light emitted by the flash tube passes through blue excitation filter 407 and impinges on the carrier tube 114. This emitted light causes certain components in the centrifuged blood sample to fluoresce. Namely, the blood plasma, and components in the buffy coat region fluoresce in response to this light. Additionally, the plug 486 in the bottom of the blood tube also fluoresces. Furthermore, at that time, the CPU 110 also controls the CCD array 128 to receive the light being emitted from the components in the blood tube. The CPU 110 receives the signals from the CCD array 128 indicative of the detection, and stores those signals.

Figure 30:
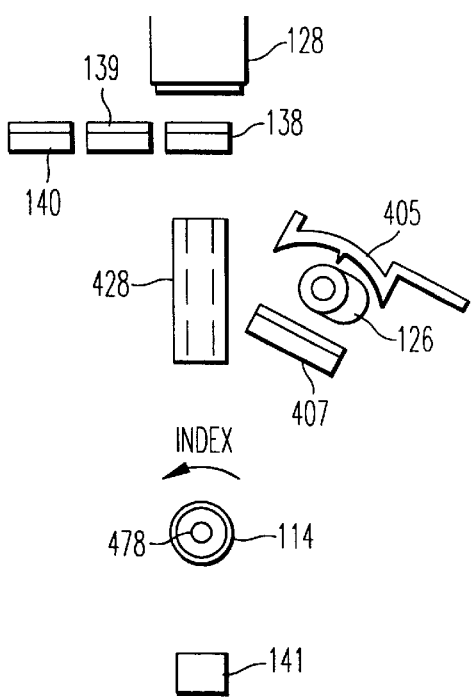
FIG. 30 is a schematic showing the indexing of the carrier tube.

In step 1160, the CPU 110 determines if the desired amount of readings have been taken with the CCD 128 array in that position and the carrier tube 114 at that orientation. If the CPU 110 determines that further reading is to be taken, the CPU 110 will proceed to step 1170 to determine if the carrier tube 114 should be indexed. If indexing is to occur, the CPU 110 proceeds to step 1180 where it performs an indexing operation as described in more detail in the aforementioned copending patent application to Michael R. Walters et al. entitled "Inertial Tube Indexer", Ser. No. 09/032,931. Specifically, the CPU controls the rotor motor 108 to cause the indexing mechanism 113 to index or rotate the carrier tube 114 in a direction indicated by arrow INDEX as shown in FIG. 30. Once this indexing process has occurred, the CPU returns to step 1150, where it controls the flash tube 126 to emit light and the CCD array 128 to receive the fluorescent light that is generated by the components in the sample tube 478 and described above.

The CPU then repeats steps 1160–1180 as described above until it determines in step 1170 that no further indexing is to occur. When the CPU 110 determines that no further indexing of the carrier tube 114 is to occur when the CCD array 128 is at this current position, the CPU proceeds to step 1190 where it determines whether all of the reading has been completed. If all of the reading has not yet been completed, the CPU proceeds to step 1200 where it moves the CCD array 128 to another position as shown, for example, in FIGS. 26 and 27. The CPU then returns to step 1150 to control the flash tube 126 and CCD array 128 to take a reading of the centrifuged sample at this new position. The processing continues through steps 1160 through 1190 to perform the desired indexing and reading as described above. If the CPU determines in step 1190 that all of the desired reading at all of the positions along the carrier tube 114 have been taken, the CPU will proceed to step 1210 where it will process the results of the readings to calculate, for example, the position of the meniscus 44 of the centrifuge sample and the plug 486 in the sample tube 478. The CPU 110 then proceeds to step 1210 to process the results as described above, and proceeds to step 1220 to perform the further reading steps described in the flow chart shown in FIG. 31.

Figure 32:
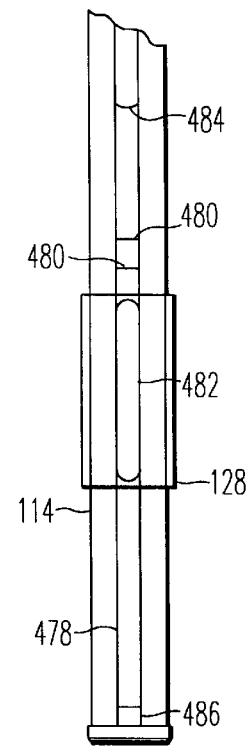
FIG. 32 is a top view of the schematic shown in FIG. 29 showing the relationship between the CCD array and carrier tube when the CPU is performing green emission readings and red emission readings.

In particular, in step 1230 the CPU 110 will control the filter motor 137 to move the filter rack 136 to position the green emission filter 138 in front of the CCD array as shown in FIG. 29B. This green emission filter will allow light having a wavelength between about 520–560 nm to pass to the CCD array 128. The CPU 110 in step 1240 controls the optical transport motor 132 to move the optical circuit assembly 322, and thus, the CCD array 128 to the appropriate position which will enable the CCD array 128 to detect light being emitted by the buffy coat region in the centrifuge blood sample. As described above in the background section of this application, the float in the blood tube will expand the buffy coat region in the blood tube. Therefore, the CPU 110 will position the CCD array 128 so that it receives light emitted from the sample in the area at which the float 482 is suspended in the sample. As discussed above, the location of the float 482 in the sample has been determined by the LED transmission readings and open fluorescence readings. This position is shown in FIG. 32.

When the CPU 110 determines from the signals provided by the rotor assembly orientation sensor 135 that the rotor assembly 106 is oriented so that the carrier tube 114 is in a position for reading, the CPU 110 in step 1250 will control the flash tube 126 to emit light. The emitted light passes through blue excitation filter 407 and impinges onto the carrier tube 114. As discussed above, this light causes the components in the centrifuge blood sample to fluoresce. In particular, the platelets and granulocytes in the buffy coat region will emit an orange color light, and the lymphocytes and monocytes in the buffy coat region will emit a green color light. The CPU 110 at that time will also control the CCD array 128 to receive the emitted light. The green emission filter 138 allows the green color light being emitted from the lymphocytes and monocytes to be received by the CCD array 128, while blocking light of other wavelengths such as the orange color light emitted by the platelets and granulocytes. The signals detected by the CCD array 128 are provided to the CPU 110 and stored.

The CPU then proceeds to step 1260 to determine if all the readings for that particular filter at that particular orientation of the carrier tube 114 has been performed. If not, the CPU returns to step 1250 and controls the flash tube 126 and CCD array 128 to obtain another reading.

Once the CPU determines in step 1260 that all the reading with that filter (i.e., the green emission filter 138) has been performed at that orientation of the carrier tube 114, the CPU proceeds to step 1270 where it determines whether all of the reading has been completed. Since this is the first reading that has been taken with the green emission filter 138 in position in front of the CCD array 128, the CPU 110 will determine that further reading with the red emission filter 139 must be performed. Hence, the CPU will proceed to step 1280 where it will control the filter motor 137 to position the red emission filter 139 in front of the CCD array 128 as shown in FIG. 29C. The red emission filter 139 allows light having a wavelength of about 621 mm and greater to pass to the CCD array 128.

The CPU will then determine in step 1290 whether it is necessary to perform an indexing of the carrier tube 114 as described above. Since no reading has yet been taken with the red emission filter 139 positioned in front of the CCD array 128, the CPU 110 will determine that no indexing is to be performed, and return to step 1250 where it will control the flash tube 126 and CCD array 128 to take a reading with the red emission filter 139 positioned in front of the CCD array 128. The CPU will then proceed to step 1260 and, if desired, repeat step 1250, until it determines in step 1260 that all reading has been performed with that particular filter. The CPU proceeds to step 1270 to determine if all desired readings have been taken. Since it determines that all desired readings have not been taken, the CPU proceeds to step 1280 where it controls the filter motor 137 to position the green emission filter 138 back in front of the CCD array 128 as shown in FIG. 29B.

The CPU then determines in step 1290 that indexing should be performed, and proceeds to step 1300 to control the rotor motor 108 to cause the indexing mechanism 113 to index or rotate the carrier tube 114 in a direction indicated by arrow INDEX as shown in FIG. 30. As stated above, this indexing process is described in more detail in the aforementioned copending patent application of Michael R. Walters et al. entitled "Inertial Tube Indexer", Ser. No. 09/032,931.

Once this indexing process has occurred, the CPU returns to step 1250 where it will take a reading of the sample with the carrier tube 114 (and hence the sample tube 478) being in this newly indexed orientation. The CPU 110 then repeats steps 1250–1300 as necessary to take the desired amount of readings with the green emission filter 138 and red emission filter 139 being positioned as shown in FIGS. 29B and 29C at each of the index orientation of the carrier tube 114.

In this example, and in the example described in the aforementioned copending U.S. patent application of Michael R. Walters entitled "Inertial Tube Indexer", Ser. No. 09/032,931, the carrier tube 114 is indexed 8 times. In other words, the carrier tube 114 is rotated by 45° for each indexing step, and green emission readings and red emission readings are taken for each of the 8 indexing positions about the circumference of the carrier tube 114. This entire process for taking red and green emission readings at each of the 8 indexed positions takes approximately 35–40 seconds.

After the red and green emission readings are all taken, the CPU 110 will determine in step 1270 that all readings have been taken. The CPU 110 will then proceed to step 1310 where it will calculate the cell counts for the platelets, granulocytes, lymphocytes and monocytes in the buffy coat region. The CPU 110 will also be able to calculate the red cell count based on the detected position of the float 282 and the plug 286. The results can be then displayed on the graphics display 146 and/or printed out by the thermal printer 148.

Although a specific order of reading and indexing is described above, the CPU 110 can be programmed to perform the readings and indexings in any suitable order.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A centrifuge for the centrifugation of fluid samples, with an integrated optical reader assembly comprising:

a carriage assembly which is adaptable to movably support an optical reader that is be adaptable to receive light emitted from the fluid sample; and an optical driver which is adaptable to control the optical reader to adapted to receive the emitted light from the fluid sample when the sample is being rotated by the centrifuge device.

2. An optical reader assembly integrated into a centrifuge, as claimed in claim 1, wherein the carriage assembly further includes a filter assembly, adaptable to substantially prohibit a portion of the emitted light having a particular wavelength from being received by the optical reader.

3. An optical reader assembly integrated into a centrifuge, as claimed in claim 2, wherein:

the filter assembly comprises a plurality of filters, each of which being adaptable to substantially prohibit a portion of the emitted light having a respective wavelength from being received by the optical reader; and the carriage assembly further comprises a filter selecting mechanism which is adaptable to select which of the filters is to be adapted to substantially prohibit the portion of the emitted light from being received by the optical reader.

4. An optical reader assembly integrated into a centrifuge, as claimed in claim 1, further comprising:

an excitation light emitting device, adaptable to emit excitation light toward the fluid sample to cause the sample to emit the emitted light in response thereto.

5. An optical reader assembly integrated into a centrifuge, as claimed in claim 1, further comprising:

a transmission light emitting device, adaptable to emit transmission light toward the fluid sample; and wherein the optical reader is further adaptable to receive a portion of the transmission light which passes through the fluid sample.

6. An optical reader assembly integrated into a centrifuge, as claimed in claim 1, further comprising:

a driving mechanism, adaptable to move the optical reader incrementally in the carriage assembly, such that the optical reader receives the emitted light from different portions of the fluid sample as the optical reader is being moved incrementally.

7. A centrifuge device comprising:

a rotor, adaptable to rotate a container which contains a fluid sample, to separate the fluid sample into a plurality of component layers in the container; and a detector device, adaptable to detect the component layers in the container while the rotor is rotating the container.

8. A centrifuge device as claimed in claim 7, further comprising:

a controller, adaptable to control a speed at which the rotor rotates the container, such that the speed at which the rotor rotates the container to separate the fluid sample into the component layers is different from the speed at which the rotor rotates the container when the detector device detects the component layers.

9. A centrifuge device as claimed in claim 7, further comprising:

a rotor orientation detector, adaptable to detect a rotational orientation of the rotor.

10. A centrifuge device as claimed in claim 9, wherein:

the rotor comprises an optical component; and the rotor orientation detector comprises an optical detector, adaptable to detect the optical component of the rotor, to detect the rotational orientation of the rotor.

11. A centrifuge device as claimed in claim 9, wherein:

the detector device is further adaptable to be controllable to detect the component layers when the rotor orientation detector detects that the rotor is at a layer detecting orientation in relation to the detector.

12. A centrifuge device as claimed in claim 7, wherein:

the rotor comprises a container holding device, adaptable to releasably mechanically couple the container to the rotor.

13. A centrifuge device as claimed in claim 12, further comprising:

an engaging device, adaptable to be positioned in an engaged position to engage the container holding device to cause the container holding device to release the container from the rotor, and to be positioned in a disengaged position to disengage the container holding device to cause the container holding device to releasably mechanically couple the container to the rotor.

14. A centrifuge device as claimed in claim 12, further comprising:

a container detector, adaptable to detect whether the container is releasably mechanically coupled to the rotor by the container holding device.

15. A centrifuge device as claimed in claim 14, wherein:

the container detector comprises:

a transmission light emitting device, adaptable to emit transmission light toward the rotor; and a container presence determiner, adaptable to detect a portion of the transmission light to determine whether the container is releasably mechanically coupled to the rotor by the container holding device.

16. A centrifuge device as claimed in claim 15, wherein:

the rotor comprises an opening therein, adaptable to allow the portion of the transmission light to pass therethrough; and the container holding device is adaptable to position the container when the container is releasably mechanically coupled to the rotor such that the portion of the transmission light is substantially prevented from being detected by the container presence determiner, to cause the container presence determiner to detect that the container is releasably mechanically coupled to the rotor.

17. A centrifuge device as claimed in claim 12, wherein:

the container holding device is adaptable to be positioned in a first position to releasably mechanically couple the container to the rotor at a proper container loading position; and the centrifuge device further comprises a container loaded detector, adaptable to detect whether the container holding device is positioned in the first position.

18. A centrifuge device as claimed in claim 17, wherein:

the rotor comprises an opening which is adaptable to allow the portion of the transmission light to pass therethrough; and the container holding device is adaptable to substantially prevent the portion of the transmission light from propagating through the opening to the container loaded detector when the container holding device is in the first position.

19. A centrifuge device as claimed in claim 7, wherein:

the detector device comprises a movable optical reader that is adaptable to receive light emitted from the fluid sample to detect the component layers.

20. A centrifuge device as claimed in claim 19, further comprising:

a controller which is adaptable to move the optical reader incrementally, such that the optical reader receives the emitted light from different portions of the fluid sample as the optical reader is being moved incrementally.

21. A centrifuge device as claimed in claim 19, wherein the detector device further comprises a filter assembly, adaptable to substantially prohibit a portion of the emitted light having a particular wavelength from being received by the optical reader.

22. A centrifuge device as claimed in claim 21, wherein:

the filter assembly comprises a plurality of filters, each of which being adaptable to substantially prohibit a portion of the emitted light having a respective wavelength from being received by the optical reader; and a filter selecting mechanism which is adaptable to select which of the filters is to be adapted to substantially prohibit the portion of the emitted light from being received by the optical reader.

23. A centrifuge device as claimed in claim 19, wherein the detector device further comprises:

an excitation light emitting device, adaptable to emit excitation light toward the fluid sample to cause the sample to emit the emitted light in response thereto.

24. A centrifuge device as claimed in claim 19, further comprising:

a transmission light emitting device, adaptable to emit transmission light toward the fluid sample; and wherein the optical reader is further adaptable to receive a portion of the transmission light which passes through the fluid sample.

* * * * *